(12) United States Patent
Murai et al.

(10) Patent No.: US 9,170,514 B2
(45) Date of Patent: Oct. 27, 2015

(54) POLYMERIZABLE MONOMER, POLYMERIC COMPOUND, CHARGE CONTROL AGENT CONTAINING THE POLYMERIC COMPOUND, AND DEVELOPER BEARING MEMBER AND TONER WHICH CONTAIN THE CHARGE CONTROL AGENT

(75) Inventors: Yasuaki Murai, Kawasaki (JP); Kei Inoue, Yokohama (JP); Ryuji Murayama, Yokohama (JP); Kazuyuki Sato, Kawasaki (JP); Masashi Hirose, Machida (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 37 days.

(21) Appl. No.: 14/006,098

(22) PCT Filed: Mar. 27, 2012

(86) PCT No.: PCT/JP2012/058778
§ 371 (c)(1),
(2), (4) Date: Sep. 18, 2013

(87) PCT Pub. No.: WO2012/133871
PCT Pub. Date: Oct. 4, 2012

(65) Prior Publication Data
US 2014/0011129 A1   Jan. 9, 2014

(30) Foreign Application Priority Data

Mar. 30, 2011  (JP) .................................. 2011-074551
Mar. 30, 2011  (JP) .................................. 2011-074835

(51) Int. Cl.
| | |
|---|---|
| *G03G 9/097* | (2006.01) |
| *C07C 233/81* | (2006.01) |
| *C07C 311/21* | (2006.01) |
| *C08F 12/22* | (2006.01) |
| *C08F 12/24* | (2006.01) |

(Continued)

(52) U.S. Cl.
CPC .......... *G03G 9/09775* (2013.01); *C07C 233/81* (2013.01); *C07C 311/21* (2013.01); *C08F 12/22* (2013.01); *C08F 12/24* (2013.01); *C08F 12/26* (2013.01); *C08F 12/30* (2013.01); *C08F 212/08* (2013.01); *C08F 212/12* (2013.01); *C08F 212/14* (2013.01); *C08F 212/32* (2013.01); *G03G 9/08706* (2013.01); *G03G 9/08708* (2013.01); *G03G 9/09733* (2013.01); *G03G 9/09758* (2013.01); *G03G 9/09766* (2013.01)

(58) Field of Classification Search
CPC .......... G03G 9/09775; G03G 9/09758; G03G 9/09733
USPC ......................................... 430/108.22, 108.4
See application file for complete search history.

(56) References Cited

U.S. PATENT DOCUMENTS

| | | | |
|---|---|---|---|
| 4,883,735 A | 11/1989 | Watanabe et al. | |
| 5,364,725 A * | 11/1994 | Wilson et al. | 430/108.4 |

(Continued)

FOREIGN PATENT DOCUMENTS

| | | |
|---|---|---|
| EP | 2 489 512 A1 | 8/2012 |
| JP | 63-184762 A | 7/1988 |

(Continued)

OTHER PUBLICATIONS

PCT International Search Report and Written Opinion of the International Searching Authority, International Application No. JP2012/058778, Mailing Date Jun. 5, 2012.

(Continued)

*Primary Examiner* — Christopher Rodee
(74) *Attorney, Agent, or Firm* — Fitzpatrick, Cella, Harper and Scinto

(57) ABSTRACT

A polymerizable monomer is provided which is represented by the following formula (1):

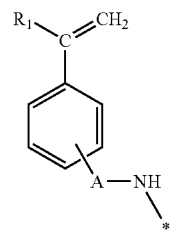

wherein $R_1$ represents a hydrogen atom or an alkyl group; A represents —CO— or —$SO_2$—; and the moiety represented by the formula (1) is, at the part shown by an asterisk *, linked to a moiety represented by the following formula (2), at any position of a, b, c or d thereof;

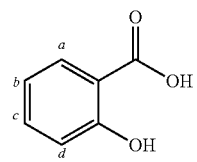

wherein the sites among a, b, c and d at which the moiety represented by the formula (2) is not linked to the moiety represented by the formula (1) each has a hydrogen atom or a substituent selected from the group consisting of an alkyl group, an alkoxy group and a sulfonic acid group, or any of which may connect at mutually adjoining positions to form a ring.

6 Claims, 6 Drawing Sheets

(51) Int. Cl.
 *C08F 12/26* (2006.01)
 *C08F 12/30* (2006.01)
 *C08F 212/08* (2006.01)
 *C08F 212/12* (2006.01)
 *C08F 212/14* (2006.01)
 *C08F 212/32* (2006.01)
 *G03G 9/087* (2006.01)

(56) References Cited

U.S. PATENT DOCUMENTS

| | | | |
|---|---|---|---|
| 5,874,194 A * | 2/1999 | Wilson et al. | 430/108.22 |
| 5,976,749 A | 11/1999 | Sukata et al. | |
| 6,399,712 B1 | 6/2002 | Seto et al. | |
| 6,916,587 B2 | 7/2005 | Fushimi et al. | |
| 7,300,991 B2 | 11/2007 | Nishimura et al. | |
| 8,883,946 B2 * | 11/2014 | Yasumatsu et al. | 430/108.4 |
| 2005/0113450 A1 * | 5/2005 | Thorarensen et al. | 514/562 |
| 2008/0187839 A1 | 8/2008 | Nishimura et al. | |
| 2014/0011130 A1 | 1/2014 | Inoue et al. | |
| 2014/0072908 A1 * | 3/2014 | Masumoto et al. | 430/108.2 |

FOREIGN PATENT DOCUMENTS

| | | |
|---|---|---|
| JP | 4-16858 A | 1/1992 |
| JP | 2694572 B2 | 12/1997 |
| JP | 10-20560 A | 1/1998 |
| JP | 10-186836 A | 7/1998 |
| JP | 2000-264931 A | 9/2000 |
| JP | 2003-5445 A | 1/2003 |
| JP | 2004-6273 A | 1/2004 |
| JP | 2005-157310 A | 6/2005 |
| JP | 2006-160854 A | 6/2006 |
| JP | 4004080 B2 | 11/2007 |
| JP | 2010-250087 A | 11/2010 |
| WO | WO 2012110359 A1 * | 8/2012 |
| WO | WO 2012157781 A1 * | 11/2012 |

OTHER PUBLICATIONS

Sonntag, "The Reactions of Aliphatic Acid Chlorides", Chem. Rev., vol. 52, No. 2, 1953, pp. 237-416.

Peyser, "Glass Transition Temperatures of Polymers", Polymer Handbook, Third Edition, 1989, pp. VI 209-VI 277.

New Experimental Chemistry Course, Fifth Edition, vol. 14, 1977, pp. 1111-1119.

European Search Report dated Sep. 5, 2014 in European Application No. 12764473.0.

Chinese Notification of Decision to Grant Patent Right dated Sep. 26, 2014 in Chinese Application No. 201280015351.9.

* cited by examiner

POLYMERIZABLE MONOMER, POLYMERIC COMPOUND, CHARGE CONTROL AGENT CONTAINING THE POLYMERIC COMPOUND, AND DEVELOPER BEARING MEMBER AND TONER WHICH CONTAIN THE CHARGE CONTROL AGENT

TECHNICAL FIELD

The present invention relates to a novel polymerizable monomer having a salicylic acid unit, and a polymeric compound produced by polymerizing the same. The present invention also relates to a charge control agent used in recording methods making use of electrophotography or the like, and a developer bearing member and a toner which contain the same.

BACKGROUND ART

In image forming methods as typified by an electrophotographic recording method, a developer charged electrostatically (hereinafter "toner") flies to the surface of a photosensitive member by electrostatic force which accords with potential differences on the photosensitive member surface, and develops electrostatic latent images formed on the photosensitive member surface. Hence, it is necessary and indispensable to control charge characteristics of the toner. Then, as a method for providing the toner with proper charge characteristics, a method is known in which a binder resin of a developer bearing member (hereinafter also "developing roller") is incorporated with a charge control agent or a method in which a charge control agent capable of providing the toner with positive charges or negative charges is mixed into toner particles to control the chargeability of the toner.

Conventionally, as negatively charging charge control agents, metal complexes of monoazo dyes, metal complexes of salicylic acid, alkylsalicylic acids or benzilic acid and so forth are used (PTL 1).

In PTL 2, it is proposed that a binder resin of a developing roller is incorporated with such a negatively charging charge control agent and this can provide a positively chargeable developer with a sufficient charge quantity by triboelectric charging.

Recently, because of safety, concern about environments and a requirement for stabler charge characteristics, it is proposed to use as the charge control agent a resin having charge control function. In PTL 3, it is proposed that a resin having a sulfonic acid group is mixed in a binder resin of the developing roller to thereby improve the developer in its uniformity of triboelectric charging and its running stability.

It is also disclosed as reported in PTL 4 that, as a polymeric charge control agent, a polymeric compound composed of a monomer unit having a sulfonic acid group is mixed into toner particles to thereby improve the charging stability of the toner and the compatibility of the compound itself with a binder resin.

Meanwhile, in recent years, images to be reproduced are desired to be of much higher image quality, and faulty images have come into question, such that "fog" occurs where the toner comes into development at blank or white areas of images and that any streaky density non-uniformity occurs on images. What is a large factor of such a phenomenon is the occurrence of a toner having come charged to a polarity reverse to the desired charge polarity.

For the purpose of making a toner charged to a reverse polarity less form or keeping the toner from being so charged, PTL 5 discloses therein an example in which a salicylic acid metal complex is used as a charge control agent, and PTL 6 discloses therein an example in which a polymeric compound composed of a monomer unit having a sulfonic acid group is used as a charge control agent. PTL 7 further discloses therein an example in which a polymeric compound to the polymeric backbone chain of which a salicylic acid unit is directly linked is used in the toner.

CITATION LIST

Patent Literature

PTL 1: Japanese Patent No. 4004080
PTL 2: Japanese Patent Application Laid-open No. H10-186836
PTL 3: Japanese Patent Application Laid-open No. 2005-157310
PTL 4: Japanese Patent Application Laid-open No. S63-184762
PTL 5: Japanese Patent Application Laid-open No. H10-020560
PTL 6: Japanese Patent Application Laid-open No. 2003-005445
PTL 7: Japanese Patent No. 2694572

SUMMARY OF INVENTION

Technical Problem

In the above charge control agents used conventionally, it can not be said for them to have any charge-providing properties that can satisfy the desires in recent years for higher speed and higher image quality, and it is sought to make further improvement or make development of a novel polymeric compound.

The present invention aims to resolve the above problems. That is, the present invention is to provide a novel polymerizable monomer that can obtain a polymeric compound having better charge-providing properties than any conventional charge control agents, and a polymeric compound obtained therefrom.

The present invention is also to provide a developer bearing member having a superior charge-providing performance to the toner inasmuch as a charge control agent containing such a polymeric compound is used in the developer bearing member.

Further, the present invention aims to provide a toner which has superior charge-providing properties including charging rise speed and saturated charge quantity, and can be made less in proportion about particles having come charged to a polarity reverse to the desired charge polarity (i.e., reversed toner).

Solution to Problem

The present invention is concerned with a polymerizable monomer represented by the following formula (1).

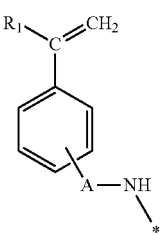

Formula (1)

In the formula (1), $R_1$ represents a hydrogen atom or an alkyl group; A represents —CO— or —$SO_2$—; and the moiety represented by the formula (1) is, at the part shown by an asterisk *, linked to a moiety represented by the following formula (2), at any position of a, b, c or d thereof.

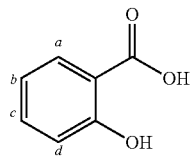

Formula (2)

In the formula (2), the sites among a, b, c and d at which the moiety represented by the formula (2) is not linked to the moiety represented by the formula (1) each has a hydrogen atom or a substituent selected from the group consisting of an alkyl group, an alkoxy group and a sulfonic acid group, or any of which may connect at mutually adjoining positions to form a ring.

The present invention is also concerned with a polymeric compound having the above monomer unit, a charge control agent containing such a polymeric compound, and a developer bearing member and a toner which contain the charge control agent.

Advantageous Effects of Invention

The present invention enables a polymeric compound to be provided which has good charge-providing properties.

The present invention also enables a charge control agent to be provided which can properly control the charge characteristics of a developer or the charge-providing performance of a developer bearing member.

The present invention still also enables a developer bearing member to be provided which has a superior charge-providing performance to the toner inasmuch as the charge control agent is used in the developer bearing member.

A toner is further provided which has good charge-providing performance about rise of charging, saturated charge quantity and so forth and can be made less in proportion about particles having come charged to a polarity reverse to the desired charge polarity, inasmuch as the above charge control agent is used as a charge control agent for toner.

Further features of the present invention will become apparent from the following description of exemplary embodiments with reference to the attached drawings.

DESCRIPTION OF EMBODIMENTS

Figure 1:
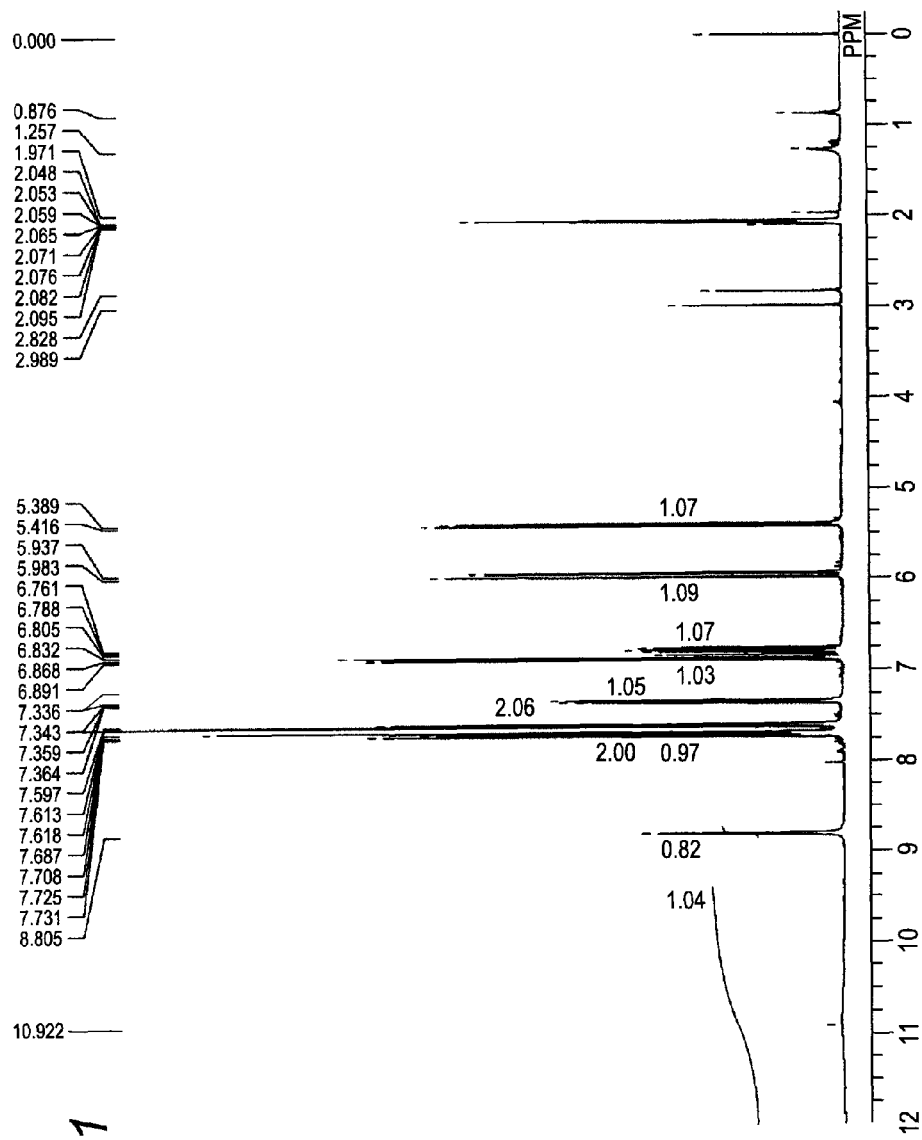
FIG. 1 is a chart showing $^1$H NMR spectrum of a polymerizable monomer (8) in acetone-$d_6$ and at room temperature and 400 MHz.

The present inventors have made extensive studies in order to resolve the above problems the prior art has had. As the result, they have discovered that a polymeric compound produced by polymerizing a polymerizable monomer represented by the following formula (1) (hereinafter simply "the formula-(1) polymerizable monomer" for convenience) and containing at least one unit represented by the following formula (3) (hereinafter simply "the formula-(3) unit" for convenience), derived from the formula-(1) polymerizable monomer, shows good charge characteristics. They have also discovered that the use of such a polymeric compound as a charge control agent in a developer bearing member can promise a high triboelectric charge-providing performance to the toner and consequently can make images obtainable which have a high image density and less "fog", and also that the incorporation of a toner with such a polymeric compound can make the toner show good charging rise and saturated charge quantity and at the same time can keep a toner from forming which may be charged to a polarity reverse to the desired charge polarity. Thus, they accomplished the Present invention.

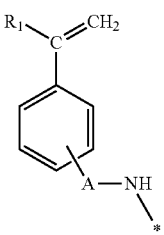

Formula (1)

In the formula (1), $R_1$ represents a hydrogen atom or an alkyl group; A represents —CO— or —SO$_2$—; and the moiety represented by the formula (1) is, at the part shown by an asterisk *, linked to a moiety represented by the following formula (2), at any position of a, b, c or d thereof.

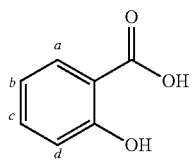

Formula (2)

In the formula (2), the sites among a, b, c and d at which the moiety represented by the formula (2) is not linked to the moiety represented by the formula (1) each has a hydrogen atom or a substituent selected from the group consisting of an alkyl group, an alkoxy group and a sulfonic acid group, or any of which may connect at mutually adjoining positions to form a ring.

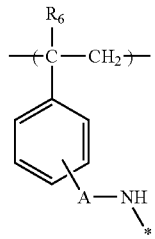

Formula (3)

In the formula (3), $R_6$ represents a hydrogen atom or an alkyl group; A represents —CO— or —SO$_2$—; and the moiety represented by the formula (3) is, at the part shown by an asterisk *, linked to a moiety represented by the following formula (2), at any position of a, b, c or d thereof.

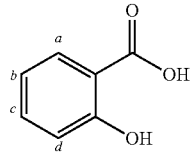

Formula (2)

In the formula (2), the sites among a, b, c and d at which the moiety represented by the formula (3) is not linked to the moiety represented by the formula (1) each has a hydrogen atom or a substituent selected from the group consisting of an alkyl group, an alkoxy group and a sulfonic acid group, or any of which may connect at mutually adjoining positions to form a ring.

The alkyl group represented by $R_1$ and $R_6$ each may include, but not particularly limited to, e.g., straight-chain, branched or cyclic alkyl groups such as a methyl group, an ethyl group, a n-propyl group, a n-butyl group, a n-pentyl group, a n-hexyl group, an isopropyl group, an isobutyl group, a sec-butyl group, a tert-butyl group and a cyclohexyl group.

As the $R_1$ and $R_6$, a case in which they are each a hydrogen atom or a methyl group is preferred from the viewpoint of the polymerizability of the polymerizable monomer.

The linking group A represents —CO— or —SO$_2$—. As the position of substitution of A, A may be linked at the o-position, m-position or p-position with respect to the vinyl group (—CR$_1$=CH$_2$) in the formula (1) or the polymeric backbone chain in the formula (3), and a case in which it is linked at the o-position is preferred in view of the readiness in obtaining raw materials and readiness in producing the monomer.

The moiety represented by the formula (1) or formula (3) is linked, at the part shown by an asterisk *, to the moiety represented by the formula (2), at any position of a, b, c or d thereof.

Where, in the formula (2), the sites among a, b, c and d at which the moiety represented by the formula (2) is not linked to the moiety represented by the formula (1) or formula (3) each have an alkyl group, the alkyl group may include, but not particularly limited to, e.g., straight-chain, branched or cyclic alkyl groups such as a methyl group, an ethyl group, a n-propyl group, a n-butyl group, a n-pentyl group, a n-hexyl group, an isopropyl group, an isobutyl group, a sec-butyl group, a tert-butyl group and a cyclohexyl group.

Where, in the formula (2), the sites among a, b, c and d at which the moiety represented by the formula (2) is not linked to the moiety represented by the formula (1) or formula (3) each have an alkoxy group, the alkoxy group may include, but not particularly limited to, e.g., straight-chain, branched or cyclic alkoxy groups such as a methoxy group, an ethoxy group, a n-propoxy group, an isopropoxy group, a n-butoxy group, an isobutoxy group, a sec-butoxy group, a tert-butoxy group and a cyclohexyloxy group.

These alkyl groups or alkoxy groups may each further be substituted, and there are no particular limitations thereon as long as the polymerizable monomer is not inhibited from being polymerizable or the polymeric compound is not extremely made low in its charge characteristics. A substituent in this case may include alkoxy groups such as a methoxy group and an ethoxy group, amino groups such as an N-methylamino group and an N,N-dimethylamino group, acyl groups such as an acetyl group, and halogen atoms such as a fluorine atom and a chlorine atom.

About the sites among a, b, c and d at which the moiety represented by the formula (2) is not linked to the moiety represented by the formula (1) or formula (3), any of them may connect at mutually adjoining positions to form a ring. For example, such a ring may include a ring formed by an alkylene group having 3 to 8 carbon atoms and a hetero ring in an alkylene chain of which an oxygen atom or a sulfur atom is present.

The above polymeric compound may be a copolymer containing at least one of each of the formula-(3) unit and a unit represented by the following formula (4).

Formula (4)

In the formula (4), $R_7$ represents a hydrogen atom or an alkyl group; and $R_8$ represents a phenyl group, a carboxyl group, a carboxylate group or a carboxylic acid amide group.

The alkyl group represented by $R_7$ may include, but not particularly limited to, e.g., straight-chain, branched or cyclic alkyl groups such as a methyl group, an ethyl group, a n-propyl group, a n-butyl group, a n-pentyl group, a n-hexyl group, an isopropyl group, an isobutyl group, a sec-butyl group, a tert-butyl group and a cyclohexyl group.

$R_7$ may preferably be a hydrogen atom or a methyl group from the viewpoint of the polymerizability of the polymerizable monomer.

The carboxylate group represented by $R_8$ may include, but not particularly limited to, e.g., ester groups such as a methyl ester group, an ethyl ester group, a n-propyl ester group, an isopropyl ester group, a n-butyl ester group, an isobutyl ester group, a sec-butyl ester group, a tert-butyl ester group, a dodecyl ester group, a 2-ethylhexyl ester group, a stearyl ester group, a phenyl ester group and a 2-hydroxyethyl ester group.

The carboxylic acid amide group represented by $R_8$ may include amide groups such as an N-methyl amide group, an N,N'-dimethyl amide group, an N,N'-diethyl amide group, an N-isopropyl amide group, an N-tert-butyl amide group and an N-phenyl amide group.

The substituent $R_8$ may further be substituted, and there are no particular limitations thereon as long as the polymerizable monomer is not inhibited from being polymerizable or the polymeric compound is not extremely made low in its charge characteristics. A substituent with which $R_8$ may be substituted may include alkoxy groups such as a methoxy group and an ethoxy group, amino groups such as an N-methylamino group and an N,N-dimethylamino group, acyl groups such as an acetyl group, and halogen atoms such as a fluorine atom and a chlorine atom.

$R_8$ may preferably be a phenyl group or a carboxylate group in view of the dispersibility and compatibility of the polymeric compound in, and with, a binder resin.

The monomer unit represented by the general formula (4) may preferably be in a content of from 0.01 mol % to 30 mol %, and much preferably from 0.01 mol % to 10 mol %, based on the whole monomer units constituting the copolymer. As long as it is within the above range, good charge characteristics can be achieved and, in addition thereto, good dispersibility and compatibility can be achieved also for the binder resin of the developer bearing member surface layer and for the binder resin of the toner.

The polymeric compound of the present invention may preferably have molecular weight in the range of from 3,000 to 100,000, and much preferably in the range of from 5,000 to 50,000, as weight-average molecular weight (Mw). As long as it has molecular weight within the above range, it can well be dispersed in the developer bearing member surface layer or in toner particle surface layers, and is well kept from coming off the developer bearing member surface or toner particle surfaces.

How to produce the polymerizable monomer of the present invention is described below in detail.

The formula-(1) polymerizable monomer may be synthesized according to a known method. An example of a synthesis scheme is shown below.

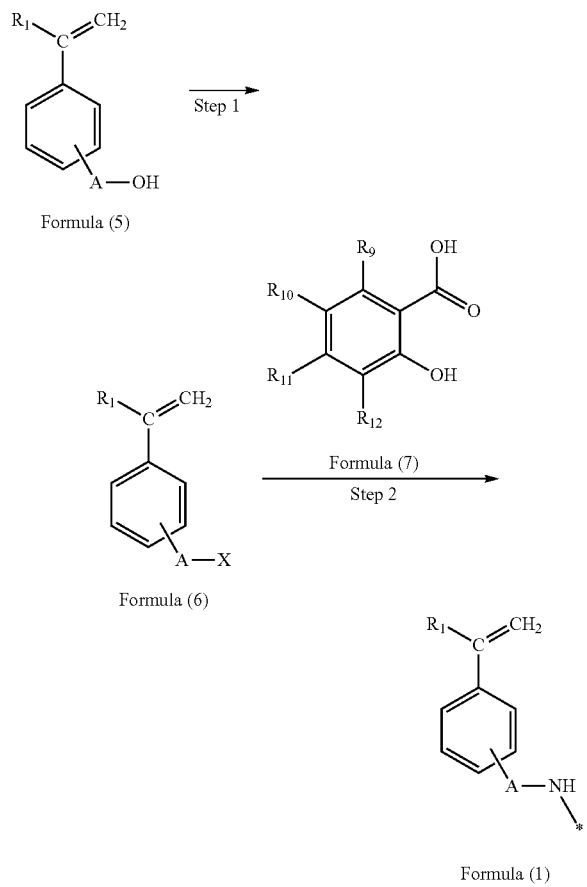

Formula (5)

Formula (7)

Formula (6)

Formula (1)

In the formulas (5) and (6) each, $R_1$ and A each represent the same as those in the formula (1). X in the formula (6) represents a halogen atom, and $R_9$ to $R_{12}$ in the formula (7) each represent the same as those corresponding to a to d, respectively, in the formula (2); provided that at least one of $R_9$ to $R_{12}$ represents an amino group.

In the synthesis scheme exemplified above, the formula-(1) polymerizable monomer may be synthesized through a step 1 in which a styrene derivative represented by the formula (5) is halogenated to obtain a formula-(6) intermediate that is an acid halide of the styrene derivative and a step 2 in which the formula-(6) intermediate is made into an amide with a formula-(7) aminosalicylic acid derivative.

The step 1 is described first. As the step 1, a known method may be utilized (see, e.g., "New Experimental Chemistry Course", Fifth Edition, Vol. 14, 1977, pp. 1111-1119). Stated specifically, the formula-(5) styrene derivative is allowed to react with a halogenating agent optionally in the presence of a solvent and a catalyst to synthesize the formula-(6) intermediate.

The formula-(5) styrene derivative is commercially available in many kinds and is obtainable with ease. It may also be synthesized by a known method.

The halogenating agent usable in the step 1 may include, e.g., thionyl halides such as thionyl chloride and thionyl bromide; phosphoryl halides such as phosphoryl chloride and phosphoryl bromide; phosphorous halides such as phosphorous pentachloride, phosphorous trichloride, phosphorous pentabromide and phosphorous tribromide; oxalyl halides such as oxalyl chloride; and also cyanuric fluoride, phosgene, triphenylphosphine-carbon tetrachloride and triphenylphosphine-carbon tetrabromide.

The halogenating agent may be used in an amount of from 1.0 mole to 30 moles, much preferably from 1.0 mole to 20 moles, and further preferably from 1.0 mole to 10 moles, per mole of the formula-(5) styrene derivative.

This step 1 may be carried out without any solvent, or may be carried out in a solvent when it is difficult to control reaction temperature or when otherwise any by-product is formed. As the solvent, there are no particular limitations thereon as long as it does not inhibit the reaction, which may include, e.g., ethers such as diethyl ether, tetrahydrofuran and dioxane; hydrocarbons such as benzene, toluene, xylene, hexane and heptane; halogen-containing hydrocarbons such as dichloromethane, dichloroethane and chloroform; amides such as N,N-dimethylformamide and N,N-dimethylimidazolidinone; nitriles such as acetonitrile and propionitrile; and sulfur-containing compounds such as dimethyl sulfoxide and sulfolane. The solvent may preferably be used in an amount determined as desired, which may preferably be in the range of from 1.0-fold by mass to 20-fold by mass based on the mass of the formula-(5) styrene derivative, from the viewpoint of production efficiency.

In the step 1, in some cases, the reaction may accelerate with appropriate addition of a catalyst. The catalyst that may be used may include, e.g., pyridine and hexamethylphosphoric triamide, any of which may preferably be used.

In the step 1, a polymerization inhibitor may be used in order to prevent the formula-(5) styrene derivative from being polymerized during the reaction. The polymerization inhibitor may include, e.g., quinones such as p-benzoquinone, naphthoquinone and 2,5-diphenyl-p-benzoquinone; polyhydric phenols such as hydroquinone, p-tert-butylcatechol and 2,5-di-tert-butylhydroquinone; and phenols such as hydroquinone monomethyl ether, di-tert-butyl-p-cresol and α-naphthol. The polymerization inhibitor may be added in an amount determined as desired, which may preferably be in the range usually of from 10 ppm to 5,000 ppm based on the formula-(5) styrene derivative.

The reaction in the step 1 is usually carried out in a temperature range of from −50° C. to 120° C., and may preferably be carried out in a temperature range of from −20° C. to 60° C. in order to prevent the formula-(5) styrene derivative from being thermally polymerized. Also, the reaction is usually completed within 24 hours.

The formula-(6) intermediate obtained in the step 1 may be used in the next step as it stands a crude product, after removing any unreacted halogenating agent, the solvent and so forth.

The step 2 is described next. As the step 2, a known method may be utilized. A typical method for the reaction may include the Shotten-Baumann method (e.g., Norman O. V. Sonntag, "Chemical Reviews", (U.S.A), American Chemical Society, 1953, Vol. 52, No. 2, pp. 237-416). Stated specifically, the formula-(6) intermediate obtained in the step 1 is allowed to react with the formula-(7) aminosalicylic acid derivative optionally in the presence of a solvent and a base to synthesize the formula-(1) polymerizable monomer.

The formula-(7) aminosalicylic acid derivative is commercially available in many kinds and is obtainable with ease. It may also be synthesized by a known method.

This step 1 may preferably be carried out without any solvent, but may preferably be carried out in a solvent in order to prevent the reaction from proceeding abruptly. There are no particular limitations on the solvent as long as it does not inhibit the reaction, which may include, e.g., water; esters such as methyl acetate, ethyl acetate and propyl acetate; ketones such as acetone and methyl ethyl ketone; ethers such as diethyl ether, tetrahydrofuran and dioxane; hydrocarbons such as benzene, toluene, xylene, hexane and heptane; and amides such as N,N-dimethylformamide and N,N-dimethylimidazolidinone. Any of these solvents may also be used in the form of a mixture of two or more types, and their mixing ratio may be determined as desired, when used mixedly. The solvent may be used in an amount determined as desired, depending on the solubility of substrate, which may preferably be in the range of from 1.0-fold by mass to 20-fold by mass based on the mass of the formula-(6) intermediate, from the viewpoint of production efficiency.

The step 2 may be carried out in a temperature range of from $-20°$ C. to $200°$ C., and may preferably be carried out in a temperature range of from $-20°$ C. to $60°$ C. in order to prevent the formula-(1) polymerizable monomer and formula-(6) intermediate from being thermally polymerized. Also, the reaction is usually completed within 24 hours.

In this step 2, a polymerization inhibitor may be used in order to prevent the formula-(1) polymerizable monomer and formula-(6) intermediate from being polymerized during the reaction. The polymerization inhibitor may include quinones such as p-benzoquinone, naphthoquinone and 2,5-diphenyl-p-benzoquinone; polyhydric phenols such as hydroquinone, p-tert-butylcatechol and 2,5-di-tert-butylhydroquinone; and phenols such as hydroquinone monomethyl ether, di-tert-butyl-p-cresol and α-naphthol. The polymerization inhibitor may be added in an amount determined as desired, which may preferably be in the range usually of from 10 ppm to 5,000 ppm based on the formula-(1) polymerizable monomer or formula-(6) intermediate.

In this step 2, hydrogen chloride formed during the reaction may be removed with a base, whereby the reaction can be accelerated. The base may include alkali hydroxides such as sodium hydroxide and potassium hydroxide, and organic bases such as pyridine, triethylamine and N,N-diisopropylethylamine. The formula-(7) aminosalicylic acid derivative may also be used in excess as the base. Any of the bases may be used in the form of a mixture of two or more types, and their mixing ratio may be determined as desired, when used mixedly. The base may be used in an equimolar amount or more, based on the formula-(6) intermediate, and may be used also as a reaction solvent.

How to produce the formula-(1) polymerizable monomer is not particularly limited to the synthesis scheme exemplified above, and may make use of, e.g., a method in which the formula-(5) styrene derivative is not made into the formula-(6) acid halide, but instead it is made into an acid anhydride, which is then made into an amide with the formula-(7) aminosalicylic acid derivative in the same way as the synthesis scheme exemplified above, or a method in which the formula-(5) styrene derivative is allowed to react with the formula-(7) aminosalicylic acid derivative together with a condensation agent to obtain the formula-(1) polymerizable monomer directly.

The compounds represented by the formulas (1) and (6), obtained in the respective steps, may be isolated and purified by a conventional process of isolation and purification of organic compounds. Such an isolation and purification process may include, e.g., recrystallization or reprecipitation, and column chromatography making use of an adsorbent such as silica gel. The purification may be carried out by any of these methods alone or in combination of two or more processes to obtain the intended compounds in a high purity.

The compounds represented by the formulas (1) and (6), obtained in the above steps, may be identified and quantitatively determined by instrumental analysis of various types. For example, any of $^1$H and $^{13}$C nuclear magnetic resonance spectroscopy (NMR), high-speed liquid chromatography (HPLC), mass spectrometry (MS) and the like may be used alone or in combination to identify and quantitatively determine the compounds.

How to produce the polymeric compound of the present invention is described below in detail.

The polymeric compound of the present invention may be produced by copolymerizing the formula-(1) polymerizable monomer with the polymerizable monomer represented by the formula (4).

As a polymerization process for the polymeric compound of the present invention, it may include radical polymerization and ionic polymerization. Living polymerization may also be used which is intended for molecular weight distribution control or structural control. It is industrially preferable to use radical polymerization.

The radical polymerization may be carried out by using a radical polymerization initiator, by irradiation with radiations, laser light or the like, by using a photopolymerization initiator and light irradiation in combination, by heating and so forth.

As the radical polymerization initiator, any agent may be used as long as it can produce radicals and initiate the polymerization reaction, and may be selected from compounds capable of producing radicals by the action of heat, light, radiation, oxidation-reduction reaction or the like. For example, it may include azo compounds, organic peroxides, inorganic peroxides, organometallic compounds and photopolymerization initiators. Stated more specifically, it may include azo compounds such as 2,2'-azobisisobutyronitrile (AIBN) and 2,2'-azobis(2,4-dimethylvaleronitrile); organic peroxides such as benzoyl peroxide (BPO), tert-butyl peroxypivarate and tert-butyl peroxyisopropyl carbonate; inorganic peroxides such as potassium persulfate and ammonium persulfate; and redox initiators such as a hydrogen peroxide-iron(II) salt type, a BPO-dimethylaniline type and a cerium (IV) salt-alcohol type. The photopolymerization initiator may include an acetophenone type, a benzoin ether type and a ketal type. Any of these radical polymerization initiators may be used in combination of two or more types.

As to polymerization temperature for the polymeric compound of the present invention, its preferable temperature range may differ depending on the type of the polymerization initiator to be used, and there are no particular limitations thereon. It is common to carry out the polymerization at a temperature of from $-30°$ C. to $180°$ C. Much preferable temperature range is from $40°$ C. to $150°$ C.

As to the amount of the polymerization initiator to be used here, it is from 0.1 part by mass to 20 parts by mass based on 100 parts by mass of the polymerizable monomers in total mass, and may preferably be so controlled that the polymeric compound having the intended molecular weight distribution can be obtained.

As the polymerization process therefor, any of processes such as solution polymerization, suspension polymerization, emulsion polymerization, dispersion polymerization, precipitation polymerization and bulk polymerization may be used, and there are no particular limitations thereon.

How to produce the polymeric compound of the present invention is not particularly limited to the production process exemplified above, and may make use of, e.g., a method in which the styrene derivative represented by the formula (5), having previously been copolymerized, and the polymerizable monomer represented by the formula (4) are halogenated and the halogenated product obtained is then made into an amide with the formula-(7) aminosalicylic acid derivative, or a method in which a copolymer of the formula-(5) styrene derivative and the formula-(4) polymerizable monomer is allowed to react with the formula-(7) aminosalicylic acid derivative together with a condensation agent to obtain the formula-(1) polymerizable monomer directly.

The polymeric compound obtained may optionally be subjected to purification treatment. There are no particular limitations on a purification process therefor, and a process such as reprecipitation or column chromatography may be used.

The structure of the polymeric compound produced may be identified by instrumental analysis of various types. For example, any of $^1H$ and $^{13}C$ nuclear magnetic resonance spectroscopy (NMR), size exclusion chromatography (SEC) and the like may be used alone or in combination to identify and quantitatively determine the compounds.

The polymeric compound of the present invention, as having superior charge-providing properties, may be incorporated in a binder resin of a developer bearing member, whereby it functions as a charge control agent that enables a developer to be provided with electric charges in a proper quantity. Also, this polymeric compound may be incorporated as a charge control agent in a toner, and this enables the toner to be controlled to have a proper charge quantity.

In the case when the present polymeric compound is used as a charge control agent of the developer bearing member, the type of the formula-(3) unit may appropriately be selected, and this enables control of the compatibility and dispersibility of the charge control agent with, and in, the binder resin of the developer bearing member.

The developer bearing member of the present invention is described below in detail.

The developer bearing member containing in its surface layer the charge control agent of the present invention can quickly provide the developer with electric charges in a proper quantity, and images are obtained which have a high image density and less fog.

The charge control agent of the present invention brings out its effect by incorporating it in the surface layer of a developing roller or developing sleeve on which the developer is to be held, without regard to the types of developing systems such as one-component development, two-component development, development making use of a magnetic developer or non-magnetic developer, and development making use of a positively chargeable developer or negatively chargeable developer. In particular, the present charge control agent acts most effectively when it is applied to a non-magnetic one-component developing system making use of a positively chargeable developer. The developer bearing member of the present invention is described below taking the case of the above developing roller.

In the above developing system, the developing roller is so disposed on a photosensitive drum as to be pressed against it and, while being rotated, develops and renders visible the electrostatic latent images formed on the developing roller, with the positively chargeable developer held on its surface. Hence, the developing roller may most preferably be so constituted as to have an elastic layer on a cylindrical shaft and also have a surface layer thereon.

The shaft of the developing roller may suffice as long as it has strength high enough to endure molding and actual service, and may preferably be made up of a rigid and electrically conductive material of from 4 mm to 10 mm in outer diameter. A material for the shaft may include, e.g., metals such as iron, aluminum, titanium, cupper and nickel; alloys containing any of these metals, such as stainless steel, duralmin, brass and bronze; and composite materials obtained by hardening carbon black or carbon fiber with a plastic.

The elastic layer of the developing roller may be formed of a known rubber material. A rubber material usable therefor may include natural rubber, silicone rubber, urethane rubber, ethylene propylene rubber, butadiene rubber, chloroprene rubber, isoprene rubber and nitrile rubber.

The elastic layer may preferably be electrically conductive, and carbon black, graphite, a metal powder, a conductive metal oxide, a conductive rubber or the like may be added thereto for the purpose of providing it with electrical conductivity.

The elastic layer may preferably have a layer thickness of from 2 mm to 10 mm. If it has a layer thickness of more than 10 mm, it may have too high resistance value, and if it has a layer thickness of less than 2 mm, it may have no sufficiently low hardness to come in low close contact with the photosensitive drum.

The surface layer of the developing roller is constituted of the charge control agent of the present invention, a conductivity-providing agent, surface-roughening particles and a binder resin.

The charge control agent may be added to the surface layer of the developing roller of the present invention in an amount of usually from 0.01 part by mass to 50 parts by mass, and preferably from 0.05 part by mass to 30 parts by mass, based on 100 parts by mass of the binder resin. As long as its amount is within the above range, the charge control agent is well achievable of both securing its charge-providing ability and keeping itself from releasing from the surface layer.

As the conductivity-providing agent usable in the surface layer, carbon black, graphite, a metal powder, a conductive metal oxide, a conductive rubber or the like may be used, as having been given as the conductivity-providing agent of the above elastic layer.

The surface-roughening particles may include, e.g., rubber particles of silicone rubber, urethane rubber, ethylene propylene rubber, butadiene rubber, chloroprene rubber, isoprene rubber, nitrile rubber or the like; elastomer particles of thermoplastic elastomers of polystyrene, polyolefin, polyvinyl chloride, polyurethane, polyester and polyamide types; resin particles of fluorine resin, silicone resin, phenol resin, naphthalene resin, furan resin, xylene resin, divinylbenzene polymer, styrene-divinylbenzene copolymer, polyacrylonitrile resin or the like; and low-density and well electrically conductive spherical carbon particles obtained by carbonizing and/or graphitizing such resin type spherical particles or mesocarbon microbeads by firing them.

As to the surface-roughening particles, its particle size distribution and amount may preferably be so controlled that the surface layer has ten-point average surface roughness (hereinafter "Rz") in the range of from 1 μm to 30 μm.

As the binder resin, there are no particular limitations thereon as long as it can follow up any flexible deformation of the elastic layer, and it may preferably be a resin which does not contaminate the photosensitive drum upon contact of the elastic layer with the photosensitive drum. For example, it may include urethane resins and fluororubber resins, having a low cross-link density and being flexible.

The surface layer of the developing roller may have a layer thickness of from 5 μm to 500 μm, and preferably from 10 μm to 200 μm. As long as its layer thickness is within the above range, the developing roller may easily secure an appropriate hardness as the roller, and may also easily secure a sufficient durability.

The developing roller of the present invention is produced by forming the elastic layer on a mandrel serving as the shaft, and thereafter coating it with a surface layer composition, followed by drying or curing.

Such a surface layer composition is one prepared by dissolving or dispersing the above charge control agent, conductivity-providing agent, surface-roughening particles and binder resin in a solvent. As the solvent usable therefor, there are no particular limitations thereon as long as it is a solvent capable of sufficiently dissolving or dispersing the materials for the surface layer composition, and any of organic solvents such as toluene, methyl ethyl ketone, ethyl acetate and isopropyl alcohol may be used.

In preparing the surface layer composition, a known dispersion machine such as a ball mill, a paint shaker, a dissolver, an attritor, a sand mill or a high-speed mill may be used, and there are no particular limitations thereon as long as it can sufficiently dissolve or disperse the materials.

The surface layer composition may be coated by a coating method such as spray coating or dipping, which may appropriately be selected in accordance with the viscosity of the surface layer composition and the layer thickness of the intended surface layer.

The toner of the present invention is described below in detail.

The toner of the present invention is a toner containing at least the above polymeric compound as a charge control agent. The use of this polymeric compound can provide a toner having a high charging rise speed, attaining a high saturated charge quantity and also making reverse-polarity toner low in proportion. Toner base particles constituting the toner of the present invention further contain toner-constituting components such as a binder resin, a colorant and a wax.

In the toner of the present invention, an optimal toner triboelectric charge quantity that accords the developing system can be controlled by the amount of the above polymeric compound to be added. The polymeric compound in the toner of the present invention may be added in an amount of usually from 0.01% by mass to 50% by mass, preferably from 0.03% by mass to 30% by mass, and much preferably from 0.05% by mass to 10% by mass, based on the total mass of the binder resin.

In the method of obtaining the toner particles directly by polymerization, the formula-(1) polymerizable monomer may be added to a toner production step together with a polymerizable monomer serving as the binder resin of the toner. In such a case, the former formula-(1) polymerizable monomer may be added in an amount usually from 0.001% by mass to 5% by mass, preferably from 0.003% by mass to 3% by mass, and much preferably from 0.005% by mass to 1% by mass, based on the total mass of the binder resin.

The toner of the present invention exhibits sufficient charge characteristics by incorporating the above polymeric compound alone, but, in accordance with the developing system in which the toner of the present invention is used, may use it in combination with any existing charge control agent for the purpose of controlling the charge characteristics. Such a charge control agent usable in combination may include, e.g., the following.

As a negatively charging charge control agent, it may include polymeric compounds having a sulfonic acid group, a sulfonic salt group or a sulfonic ester group; salicylic acid derivatives and metal complexes thereof; monoazo metal compounds; acetylacetone metal compounds; aromatic hydroxycarboxylic acids, aromatic mono- and polycarboxylic acids, and metal salts, anhydrides or esters thereof; phenol derivatives such as bisphenol; and also urea derivatives, boron compounds and carixarene.

As a positively charging charge control agent, it may include Nigrosine and Nigrosine-modified products, modified with a fatty acid metal salt or the like; guanidine compounds; imidazole compounds; quaternary ammonium salts such as tributylbenzylammonium 1-hydroxy-4-naphthosulfonate and tetrabutylammonium tetrafluoroborate, and analogues of these, including onium salts such as phosphonium salts, and lake pigments of these; triphenylmethane dyes and lake pigments of these (lake-forming agents may include tungstophosphoric acid, molybdophosphoric acid, tungstomolybdophosphoric acid, tannic acid, lauric acid, gallic acid, ferricyanides and ferrocyanides); metal salts of higher fatty acids; diorganotin oxides such as dibutyltin oxide, dioctyltin oxide and dicyclohexyltin oxide; and diorganotin borates such as dibutyltin borate, dioctyltin borate and dicyclohexyltin borate.

The components constituting the toner of the present invention are described below in detail.

As the binder resin usable in the toner of the present invention, a known resin may be used, where usable are a vinyl resin such as styrene-acrylic resin, a polyester resin, and a hybrid resin formed of combination of these.

In the method of obtaining the toner particles directly by polymerization, monomer(s) for forming them is/are used. Such monomer(s) may specifically include styrene; styrene monomers such as o-, m- or p-methylstyrene, and o-, m- or p-ethylstyrene; acrylate monomers such as methyl acrylate, ethyl acrylate, propyl acrylate, butyl acrylate, octyl acrylate, dodecyl acrylate, stearyl acrylate, behenyl acrylate, 2-ethylhexyl acrylate, dimethylaminoethyl acrylate, diethylaminoethyl acrylate, acrylonitrile and acrylic acid amide; methacrylate monomers such as methyl methacrylate, ethyl methacrylate, propyl methacrylate, butyl methacrylate, octyl methacrylate, dodecyl methacrylate, stearyl methacrylate, behenyl methacrylate, 2-ethylhexyl methacrylate, dimethylaminoethyl methacrylate, diethylaminoethyl methacrylate, methacrylonitrile and methacrylic acid amide; and olefinic monomers such as butadiene, isoprene and cyclohexene.

Any of these may be used alone, or may commonly be used in the form of an appropriate mixture of monomers which are so mixed that the theoretical glass transition temperature (Tg) as described in "POLYMER HANDBOOK" Edited by J. Brandrup and E. H. Immergut, (U.S.A.), Third Edition, John Wiley & Sons, Inc., 1989, pp. 209-277, may stand in the range of from 40° C. to 75°. If the theoretical glass transition temperature is less than 40° C., a problem tends to arise in view of the storage stability or running stability of the toner. If on the other hand it is more than 75° C., images may be of low transparency when full-color images of toners are formed.

The binder resin in the toner of the present invention makes use of a non-polar resin such as polystyrene in combination with a polar resin such as polyester resin or polycarbonate resin, and this enables control of in-toner distribution of additives such as a colorant, the charge control agent and a wax. For example, in the case when the toner particles are directly produced by suspension polymerization, the polar resin is added at the time of polymerization reaction that extends from a dispersion step up to a polymerization step. The polar resin is added in accordance with a balance between the polarity of a polymerizable monomer composition made into toner particles and that of an aqueous medium. As the result, this enables the reaction to be so controlled that the polar resin may form thin layers on the surfaces of toner particles or may be present in toner particles with gradation from their surfaces toward centers. Here, such a polar resin that may have mutual action with the colorant or the formula-(1) polymerizable monomer may be used, whereby the state of presence of the colorant can be made into a desirable form.

Further, in the present invention, in order to enhance the mechanical strength of the toner particles and also control the molecular weight of the binder resin, a cross-linking agent may also be used when the binder resin is synthesized.

As the cross-linking agent used in the toner of the present invention, it may include, as a bifunctional cross-linking agent, divinylbenzene, 2,2-bis(4-acryloxyethoxyphenyl)propane, 2,2-bis(4-methacryloxyphenyl)propane, diallyl phthalate, ethylene glycol diacrylate, 1,3-butylene glycol diacrylate, 1,4-butanediol diacrylate, 1,5-pentanediol diacrylate, 1,6-hexanediol diacrylate, neopentyl glycol diacrylate, diethylene glycol diacrylate, triethylene glycol diacrylate, tetraethylene glycol diacrylate, polyethylene glycol #200 diacrylate, polyethylene glycol #400 diacrylate, polyethylene glycol #600 diacrylate, dipropylene glycol diacrylate, polypropylene glycol diacrylate, polyester type diacrylates, and the above diacrylates each acrylate moiety of which has been replaced with methacrylate.

As a polyfunctional cross-linking agent, it may include pentaerythritol triacrylate, trimethylolethane triacrylate, trimethylolpropane triacrylate, tetramethylolmethane tetraacrylate, oligoester acrylate, and methacrylates of these, and also triallyl cyanurate, triallyl isocyanurate and triallyl trimellitate.

Any of these cross-linking agents may preferably be used in an amount of from 0.05 part by mass to 10 parts by mass, and much preferably from 0.1 part by mass to 5 parts by mass, based on 100 parts by mass of the above monomer, in view of the fixing performance and anti-offset properties of the toner.

The toner of the present invention may be either of a magnetic toner and a non-magnetic toner. Where it is used as the magnetic toner, a magnetic material which may include the following may preferably be used. That is, it may include iron oxides such as magnetite, maghemite and ferrite, or iron oxides including other metal oxides; metals such as Fe, Co and Ni, or alloys of any of these metals with any of metals such as Al, Co, Cu, Pb, Mg, Ni, Sn, Zn, Sb, Be, Bi, Cd, Ca, Mn, Se, Ti, W and V, and mixtures of any of these.

The magnetic material may specifically include, e.g., triiron tetraoxide ($Fe_3O_4$), γ-iron sesquioxide (γ-$Fe_2O_3$), zinc iron oxide ($ZnFe_2O_4$), yttrium iron oxide ($Y_3Fe_5O_{12}$), cadmium iron oxide ($CdFe_2O_4$), gadolinium iron oxide ($Gd_3Fe_5O_{12}$), copper iron oxide ($CuFe_2O_4$), lead iron oxide ($PbFe_{12}O_{19}$), nickel iron oxide ($NiFe_2O_4$), neodymium iron oxide ($NdFe_2O_3$), barium iron oxide ($BaFe_{12}O_{19}$), magnesium iron oxide ($MgFe_2O_4$), manganese iron oxide ($MnFe_2O_4$), lanthanum iron oxide ($LaFeO_3$), iron powder (Fe), cobalt powder (Co) and nickel powder (Ni). Any of the above magnetic materials may be used alone or in combination of two or more types. A magnetic material particularly preferable for what is aimed in the present invention is fine powder of triiron tetraoxide or γ-iron sesquioxide.

These magnetic materials may be those having an average particle diameter of from 0.1 μm to 2 μm (preferably from 0.1 μm to 0.3 μm), and a coercive force of from 1.6 kA/m to 12 kA/m, a saturation magnetization of from 5 $Am^2$/kg to 200 $Am^2$/kg (preferably from 50 $Am^2$/kg to 100 $Am^2$/kg) and a residual magnetization of from 2 $Am^2$/kg to 20 $Am^2$/kg, as magnetic properties under application of a magnetic field of 795.8 kA/m, which are preferable in view of the developing performance of the toner.

Any of these magnetic materials may be added in an amount of from 10 parts by mass to 200 parts by weight, and preferably from 20 parts by mass to 150 parts by weight, based on 100 parts by weight of the binder resin.

Where on the other hand the toner is used as the non-magnetic toner, any known colorant including conventionally known various dyes or pigments may be used as the colorant.

For example, as a colorant for magenta, it may include, e.g., C.I. Pigment Red 1, C.I. Pigment Red 2, C.I. Pigment Red 3, C.I. Pigment Red 4, C.I. Pigment Red 5, C.I. Pigment Red 6, C.I. Pigment Red 7, C.I. Pigment Red 8, C.I. Pigment Red 9, C.I. Pigment Red 10, C.I. Pigment Red 11, C.I. Pigment Red 12, C.I. Pigment Red 13, C.I. Pigment Red 14, C.I. Pigment Red 15, C.I. Pigment Red 16, C.I. Pigment Red 17, C.I. Pigment Red 18, C.I. Pigment Red 19, C.I. Pigment Red 21, C.I. Pigment Red 22, C.I. Pigment Red 23, C.I. Pigment Red 30, C.I. Pigment Red 31, C.I. Pigment Red 32, C.I. Pigment Red 37, C.I. Pigment Red 38, C.I. Pigment Red 39, C.I. Pigment Red 40, C.I. Pigment Red C.I. Pigment Red 41, C.I. Pigment Red 48, C.I. Pigment Red 49, C.I. Pigment Red 50, C.I. Pigment Red 51, C.I. Pigment Red 52, C.I. Pigment Red 53, C.I. Pigment Red 54, C.I. Pigment Red 55, C.I. Pigment Red 57, C.I. Pigment Red 58, C.I. Pigment Red 60, C.I. Pigment Red 63, C.I. Pigment Red 64, C.I. Pigment Red 68, C.I. Pigment Red 81, C.I. Pigment Red 83, C.I. Pigment Red 87, C.I. Pigment Red 88, C.I. Pigment Red 89, C.I. Pigment Red 90, C.I. Pigment Red 112, C.I. Pigment Red 114, C.I. Pigment Red 122, C.I. Pigment Red 123, C.I. Pigment Red 163, C.I. Pigment Red 202, C.I. Pigment Red 206, C.I. Pigment Red 207, C.I. Pigment Red 209; C.I. Pigment Violet 19; and C.I. Vat Red 1, C.I. Vat Red 2, C.I. Vat Red 10, C.I. Vat Red 13, C.I. Vat Red 15, C.I. Vat Red 23, C.I. Vat Red 29, C.I. Vat Red 35.

As a colorant for cyan, it may include, e.g., C.I. Pigment Blue 2, C.I. Pigment Blue 3, C.I. Pigment Blue 15:1, C.I. Pigment Blue 15:3, C.I. Pigment Blue 16, C.I. Pigment Blue 17, C.I. Pigment Blue 25, C.I. Pigment Blue 26; C.I. Vat Blue 6; C.I. Acid Blue 45; and copper phthalocyanine pigments the phthalocyanine skeleton of which has been substituted with 1 to 5 phthalimide methyl group(s).

As a colorant for yellow, it may include, e.g., C.I. Pigment Yellow 1, C.I. Pigment Yellow 2, C.I. Pigment Yellow 3, C.I. Pigment Yellow 4, C.I. Pigment Yellow 5, C.I. Pigment Yellow 6, C.I. Pigment Yellow 7, C.I. Pigment Yellow 10, C.I. Pigment Yellow 11, C.I. Pigment Yellow 12, C.I. Pigment Yellow 13, C.I. Pigment Yellow 14, C.I. Pigment Yellow 15, C.I. Pigment Yellow 16, C.I. Pigment Yellow 17, C.I. Pigment Yellow 23, C.I. Pigment Yellow 65, C.I. Pigment Yellow 73, C.I. Pigment Yellow 74, C.I. Pigment Yellow 83, C.I. Pigment Yellow 93, C.I. Pigment Yellow 155, C.I. Pigment Yellow 180; C.I. Solvent Yellow 9, C.I. Solvent Yellow 17, C.I. Solvent Yellow 24, C.I. Solvent Yellow 31, C.I. Solvent Yellow 35, C.I. Solvent Yellow 58, C.I. Solvent Yellow 93, C.I. Solvent Yellow 100, C.I. Solvent Yellow 102, C.I. Solvent Yellow 103, C.I. Solvent Yellow 105, C.I. Solvent Yellow 112, C.I. Solvent Yellow 162, C.I. Solvent Yellow 163; and C.I., Vat Yellow 1, C.I., Vat Yellow 3, C.I., Vat Yellow 20.

As a black colorant, e.g., carbon black, aniline black, acetylene black and a colorant toned in black by the use of yellow, magenta and cyan colorants shown above may be used.

Any of these colorants may suitably be used in an amount, which may differ depending on the types of the colorants, of from 0.1 part by mass to 60 parts by mass, and preferably from 0.5 part by mass to 50 parts by mass, in total mass based on 100 parts by mass of the binder resin.

As the wax component usable in the present invention, it may specifically include petroleum waxes such as paraffin wax, microcrystalline wax and petrolatum, and derivatives thereof; montan wax and derivatives thereof; hydrocarbon waxes obtained by Fischer-Tropsch synthesis, and derivatives thereof; polyolefin waxes as typified by polyethylene wax, and derivatives thereof; and naturally occurring waxes such as carnauba wax and candelilla wax, and derivatives thereof. The derivatives of these include oxides, block copolymers with vinyl monomers, and graft modified products. It may further include alcohols such as higher aliphatic alcohols, fatty acids such as stearic acid and palmitic acid, acid amides or fatty esters of these compounds, hardened caster oil and derivatives thereof, vegetable waxes, and animal waxes. Any of these may be used alone or in combination.

The wax component may preferably be added in such an amount that its content based on 100 parts by mass of the binder resin is from 2.5 parts by mass to 15.0 parts by mass, and much preferably from 3.0 parts by mass to 10.0 parts by mass, in total mass.

To the toner of the present invention, an inorganic fine powder may externally be added to the toner base particles as a fluidizing agent. As the fluidizing agent, fine powders of, e.g., silica, titanium oxide, alumina, double oxides of any of them, and any of these having been surface-treated may be used.

In the present invention, the toner may preferably have a weight-average particle diameter (D4) of from 3.0 µm to 15.0 µm, and much preferably from 4.0 µm to 12.0 µm, from the viewpoint of securing the stability of charging and obtaining images with high image quality.

The toner of the present invention may also have a ratio of weight-average particle diameter D4 to number-average particle diameter D1 (hereinafter "weight-average particle diameter D4/number-average particle diameter D1" or "D4/D1"), of 1.35 or less, and preferably 1.30 or less.

Incidentally, the weight-average particle diameter D4 and number-average particle diameter D1 of the toner of the present invention may differ in how to control them, depending on how to produce the toner particles. For example, in the case of suspension polymerization, they may be controlled by controlling the concentration of a dispersant used when an aqueous dispersion medium is prepared, the rate of reaction and stirring, the time for reaction and stirring, and so forth.

The toner particles in the present invention may be produced by using whatever method, and may preferably be obtained by a production process in which granulation is carried out in an aqueous medium, such as a suspension polymerization process or a suspension granulation process. Where toner particles are produced by any commonly available pulverization process, it involves a very high degree of technical difficulty in view of developing performance to add the wax component in a large quantity to toner particles. That the toner particles are obtained by granulation in an aqueous medium enables enclosure of the wax component in the particles, and can keep the wax component from coming exposed to the surfaces of toner particles even when the wax component is used in a large quantity.

The suspension polymerization process is one of the most preferable production processes in view of long-term developing stability in virtue of the enclosure of the wax component in the toner particles and in view of production cost such that any solvent is not used. Further, the particle shape of the toner is precisely controlled, and this enables enclosure of the colorant in individual toner particles in equal content. Hence, any effect on charge characteristics by the colorant can be uniform, and this brings a well balanced improvement in developing performance and transfer performance of the toner.

Meanwhile, the suspension granulation process does not have any heating step in its production steps. Hence, the resin and the wax component can be kept from coming compatibilized with each other, which may otherwise be compatibilized when a low-melting wax is used, thus the toner can be prevented from having a low glass transition temperature because of their coming compatibilized. In addition, the choices of toner materials making up the binder resin can be broad, and also it is easy to use as a chief component the polyester resin, which is commonly considered advantageous for fixing performance. Hence, this is a production process that is advantageous when a toner is produced which has resin composition to which the suspension polymerization process is not applicable.

In the case when the toner is produced by the suspension polymerization process, the polymeric compound of the present invention (or the polymerizable monomer of the present invention), the polymerizable monomer making up the binder resin, the colorant, the wax component, a polymerization initiator and so forth are mixed to prepare a polymerizable monomer composition, then the polymerizable monomer composition is dispersed in an aqueous medium to granulate the polymerizable monomer composition to form its particles, and thereafter polymerizing the polymerizable monomer in the particles of the polymerizable monomer composition to obtain toner particles. Here, it is preferable that the polymerizable monomer composition is a composition prepared by mixing a fluid dispersion obtained by dispersing the colorant in a first polymerizable monomer (or a portion of the polymerizable monomer), with at least a second polymerizable monomer (or the remaining polymerizable monomer). That is, the colorant is made to stand sufficiently dispersed in the first polymerizable monomer and thereafter the resultant fluid dispersion is mixed with the second polymerizable monomer together with the other toner materials. This can make the colorant present in the interior of the toner particles in a better dispersed state.

As the polymerization initiator used in the above suspension polymerization process, it may include known polymerization initiators, and may include, e.g., azo compounds, organic peroxides, inorganic peroxides, organometallic compounds and photopolymerization initiators. Stated more specifically, it may include azo type polymerization initiators such as 2,2'-azobis(isobutyronitrile), 2,2'-azobis(2-methylbutyronitrile), 2,2'-azobis(4-methoxy-2,4-dimethylvaleronitrile, 2,2'-azobis(2,4-dimethylvaleronitrile) and dimethyl 2,2'-azobis(isobutyrate); organic peroxide type polymerization initiators such as benzoyl peroxide, di-tert-butyl peroxide, tert-butyl peroxyisopropyl monocarbonate, tert-hexyl peroxybenzoate and tert-butyl peroxybenzoate; inorganic peroxide type polymerization initiators such as potassium persulfate and ammonium persulfate; and redox initiators such as a hydrogen peroxide-ferrous salt type, BPO-dimethylaniline type and a cerium(IV) salt-alcohol type. The photopolymerization initiator may include an acetophenone type, a benzoin ether type and a ketal type. Any of these polymerization initiators may be used in combination of two or more types.

The above polymerization initiator may preferably be in a concentration in the range of from 0.1 part by mass to 20 parts by mass, and much preferably from 0.1 part by mass to 10 parts by mass, based on 100 parts by mass of the polymerizable monomer. The polymerization initiator may a little vary in type depending on methods for polymerization, and may be used alone or in the form of a mixture, making reference to its 10-hour half-life period temperature.

The aqueous medium used in the suspension polymerization process may preferably be incorporated with a dispersion stabilizer. As the dispersion stabilizer, any known inorganic or organic dispersion stabilizer may be used. The inorganic dispersion stabilizer may include, e.g., calcium phosphate, magnesium phosphate, aluminum phosphate, zinc phosphate, magnesium carbonate, calcium carbonate, calcium hydroxide, magnesium hydroxide, aluminum hydroxide, calcium metasilicate, calcium sulfate, barium sulfate, bentonite, silica and alumina. The organic dispersion stabilizer may include, e.g., polyvinyl alcohol, gelatin, methyl cellulose, methyl hydroxypropyl cellulose, ethyl cellulose, carboxymethyl cellulose sodium salt, and starch.

A nonionic, anionic or cationic surface active agent may also be used as the dispersion stabilizer. For example, it may include sodium dodecyl sulfate, sodium tetradecyl sulfate, sodium pentadecyl sulfate, sodium octyl sulfate, sodium oleate, sodium laurate, potassium stearate, and calcium oleate.

Of the above dispersion stabilizers, it is preferable in the present invention to use an inorganic sparingly water-soluble dispersion stabilizer that is soluble in acids. Also, in the present invention, where an aqueous dispersion medium is prepared using the sparingly water-soluble dispersion stabilizer, such a dispersion stabilizer may preferably be used in such a proportion that it is in an amount ranging from 0.2 part by mass to 2.0 parts by mass based on 100 parts by mass of the polymerizable monomer. This is preferable in view of the stability of droplets in the aqueous dispersion medium of the polymerizable monomer composition. In the present invention, the aqueous dispersion medium may also preferably be prepared with use of water in an amount ranging from 300 parts by mass to 3,000 parts by mass based on 100 parts by mass of the polymerizable monomer composition.

In the present invention, where the aqueous dispersion medium in which the sparingly water-soluble inorganic dispersion stabilizer has been dispersed is prepared, it may be dispersed using a commercially available dispersion stabilizer as it is. In order to obtain particles of the dispersion stabilizer which have a fine and uniform particle size, the sparingly water-soluble inorganic dispersion stabilizer may be prepared by forming it in a liquid medium such as water with high-speed stirring. For example, where tricalcium phosphate is used as the dispersion stabilizer, an aqueous sodium phosphate solution and an aqueous calcium chloride solution may be mixed under high-speed stirring to form fine particles of the tricalcium phosphate, whereby a preferable dispersion stabilizer can be obtained.

In the case when the toner is produced by the suspension granulation process, the toner is produced in the following way, for example. First, the polymeric compound of the present invention, the binder resin, the colorant, the wax component and so forth are mixed in a solvent to prepare a solvent composition. Next, the solvent composition is dispersed in an aqueous medium to granulate the solvent composition to form its particles therein to obtain a toner particle suspension. Then, the suspension obtained is heated or put under reduced pressure to remove the solvent, thus toner particles can be obtained.

It is preferable that the solvent composition in the above step is a composition prepared by mixing a fluid dispersion obtained by dispersing the colorant in a first solvent, with a second solvent. That is, the colorant is more sufficiently dispersed in the first solvent and thereafter the resultant fluid dispersion is mixed with the second solvent together with the other toner materials. This can make the colorant present in the interior of the toner particles in a better dispersed state.

As the solvent used in the above suspension granulation process, it may include, e.g., hydrocarbons such as toluene, xylene and hexane; halogen-containing hydrocarbons such as methylene chloride, chloroform, dichloroethane, trichloroethane and carbon tetrachloride; alcohols such as methanol, ethanol, butanol and isopropyl alcohol; polyhydric alcohols such as ethylene glycol, propylene glycol, diethylene glycol and triethylene glycol; Cellosolves such as methyl Cellosolve and ethyl Cellosolve; ketones such as acetone, methyl ethyl ketone and methyl isobutyl ketone; ethers such as benzyl alcohol ethyl ether, benzyl alcohol isopropyl ether and tetrahydrofuran; and esters such as methyl acetate, ethyl acetate and butyl acetate. Any of these may be used alone or in the form of a mixture of two or more types. Of these, in order to readily remove the solvent in the toner particle suspension, it is preferable to use a solvent having a low boiling point and capable of dissolving the binder resin sufficiently.

The solvent may preferably be used in an amount ranging from 50 parts by mass to 5,000 parts by mass, and much preferably from 120 parts by mass to 1,000 parts by mass, based on 100 parts by mass of the binder resin.

The aqueous medium used in the suspension granulation process may preferably be incorporated with a dispersion stabilizer. As the dispersion stabilizer, any known inorganic or organic dispersion stabilizer may be used. The inorganic dispersion stabilizer may include calcium phosphate, calcium carbonate, aluminum hydroxide, calcium sulfate and barium carbonate. The organic dispersion stabilizer may include, e.g., water-soluble polymers such as polyvinyl alcohol, methyl cellulose, hydroxyethyl cellulose, ethyl cellulose, carboxymethyl cellulose sodium salt, sodium polyacrylate and sodium polymethacrylate; and surface active agents as exemplified by anionic surface active agents such as sodium dodecylbenzene sulfonate, sodium octadecyl sulfate, sodium oleate, sodium laurate and potassium stearate; cationic surface active agents such as laurylamine acetate, stearylamine acetate and lauryl trimethylammonium chloride; amphoteric surface active agents such as lauryl dimethylamine oxide; and nonionic surface active agents such as polyoxyethylene alkyl ethers, polyoxyethylene alkyl phenyl ethers and polyoxyethylene alkyl amines.

The dispersion stabilizer may be used in an amount ranging from 0.01 part by mass to 20 parts by mass based on 100 parts by mass of the binder resin.

Measuring methods used in working examples given later are described below.

(1) Compositional Analysis:

Structures of the formula-(1) polymerizable monomer and polymeric compound composed of the same polymerizable monomer are determined by using the following instrument.

$^1$H, $^{13}$C NMR:

Using ECA-400 (400 MHz), manufactured by JEOL Ltd., measurement by nuclear magnetic resonance spectroscopy (NMR) is made at 25° C. in a deuterated solvent containing tetramethylsilane as an internal standard substance. The values of chemical shifts are shown as ppm shift values (5 values) assuming the value of the internal standard substance tetramethylsilane as 0. MS:

Analysis by mass spectrometry is made using LC/MSD TOF, manufactured by Agilent Technologies Inc. Here, as ionization, electrospray ionization (ESI) is used.

(2) Purity Measurement:

The purity of the formula-(1) polymerizable monomer is measured by using the following instrument.

Instrument: HPLC LC-20A, manufactured by Shimadzu Corporation.

Column: INERTSIL ODS-3 (available from GL Sciences, Inc.).

Eluent: Aqueous methanol-0.1% trifluoroacetic acid solution).

Flow rate: 1.0 ml/min.

Oven temperature: 40° C.

Amount of sample injected: 1.0 μl.

(3) Measurement of Molecular Weight:

The molecular weight of the polymeric compound composed of the formula-(1) polymerizable monomer is measured by size exclusion chromatography (SEC), and calculated in terms of standard polystyrene. The measurement of molecular weight by SEC is made as shown below.

A sample is added to the following eluting solution in such a way as for the sample to be in a concentration of 1.0% by mass, and the solution obtained and having been left to stand at room temperature for 24 hours is filtered with a solvent-resistant membrane filter of 0.2 μm in pore diameter to make up a sample solution.

The measurement is made under the following conditions.

Instrument: High-speed GPC instrument "HLC-8220 GPC" (manufactured by Tosoh Corporation).

Columns: Combination of two columns, ASAHIPAK GF-510HQ and GF-310HQ (available from Showa Denko K.K.).

Eluent: DMF (20 mmol/l, containing lithium bromide).

Flow rate: 0.6 ml/min.

Oven temperature: 40° C.

Amount of sample injected: 0.10 ml.

To calculate the molecular weight distribution of the sample, a molecular weight calibration curve is used which is prepared using a standard polystyrene resin (TSK Standard Polystyrene Resin F-850, F-450, F-288, F-128, F-80, F-40, F-20, F-10, F-4, F-2, F-1, A-5000, A-2500, A-1000, A-500; available from Tosoh Corporation).

(4) Measurement of Acid Value:

The acid value of the polymeric compound composed of the formula-(1) polymerizable monomer is determined in the following way.

Basic operation is made according to JIS K-0070.

1) A sample is precisely weighed in an amount of from 0.5 g to 2.0 g. The mass at this point is represented by W (g).

2) The sample is put into a 50 ml beaker, and 25 ml of a toluene/ethanol (2/1) mixed solvent is added thereto to dissolve the sample.

3) Using an ethanol solution of 0.1 mol/l KOH, it is titrated by using a potential difference titration measuring instrument (e.g., an automatic titration measuring instrument "COM-2500", manufacture by Hiranuma Sangyo Co., Ltd. may be used).

4) The amount of the KOH solution used at this point is represented by S (ml). A blank is measured simultaneously, and the amount of the KOH at this point is represented by B (ml).

5) The acid value is calculated according to the following expression. Here, f is the factor of the KOH solution.

$$\text{Acid value (mgKOH/g)} = \{(S-B) \times f \times 5.61\}/W.$$

EXAMPLES

The present invention is described below in greater detail by giving Examples and Comparative Examples, to which, however, the present invention is by no means limited as long as they are not beyond the gist of the invention. In the following description, "part(s)" and "%" are by mass unless particularly noted.

Example 1

Formula-(1) polymerizable monomers were produced in the following way.

Production Example of Polymerizable Monomer (8)

A polymerizable monomer (8) represented by the following structural formula (8) was produced according to the following scheme.

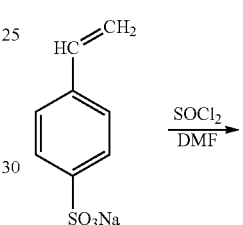

Formula (18)

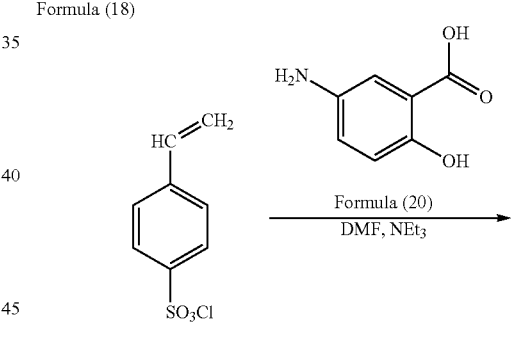

Formula (19)

Formula (20)

Formula (8)

Into a reaction vessel fitted with a cooling pipe, a stirrer, a thermometer and a nitrogen feed pipe, 2.0 parts of 4-tert-butylcatechol, 565 parts of thionyl chloride and 400 parts of dehydrated N,N-dimethylformamide were fed, and then stirred under ice cooling. To the solution obtained, while this was kept at 0° C. or below, 150 parts of formula-(18) sodium p-styrenesulfonate was dividedly added thereto. After its addition, the reaction solution was stirred for 24 hours while keeping the liquid temperature. After the reaction was completed, the reaction solution was poured into 1,500 parts of water to carry out extraction with toluene, and the organic layer formed was washed with ion-exchanged water. This organic layer was then dried with sodium sulfuric anhydride, followed by evaporation of the solvent under reduced pressure to obtain 128 parts (quantitative) of formula-(19) p-styrenesulfonic acid chloride.

Into a reaction vessel fitted with a cooling pipe, a stirrer, a thermometer and a nitrogen feed pipe, 15 parts of formula-(20) 5-aminosalicylic acid, 142 parts of dehydrated N,N-dimethylformamide and 11 parts of triethylamine were fed, and then stirred under ice cooling. To the solution obtained, while this was kept at 5° C. or below, a solution beforehand prepared by dissolving in 15 parts of chloroform 21 parts of the formula-(19) p-styrenesulfonic acid chloride obtained above was dropwise added. After its addition made dropwise was completed, the liquid temperature was slowly returned to room temperature, where the reaction was carried out for 4 hours. After the reaction was completed, 270 parts of ethyl acetate was added, and the organic layer formed was washed with an aqueous 1 mol/liter hydrochloric acid solution and with ion-exchanged water. This organic layer was then dried with sodium sulfuric anhydride, followed by concentration of the solvent under reduced pressure and then reprecipitation with n-heptane. Thereafter, the precipitate formed was separated by filtration to obtain 26 parts of the polymerizable monomer (8) (yield: 83%).

That the polymerizable monomer obtained had the structure represented by the above formula was identified by using the instruments described previously. The results of analysis are shown below.

Results of Analysis of Polymerizable Monomer (8)
(1) Results of $^1$H NMR (400 MHz, acetone-$d_6$, 25° C.) (see FIG. 1):
δ [ppm]=10.92 (brs, 1H), 8.81 (s, 1H), 7.73 (d, 1H), 7.70 (d, 2H), 7.61 (d, 2H), 7.35 (dd, 1H), 6.88 (d, 1H), 6.80 (dd, 1H), 5.96 (d, 1H), 5.40 (d, 1H).
(2) Results of $^{13}$C NMR (100 MHz, acetone-$d_6$, 25° C.)
δ [ppm]=172.0, 160.7, 142.7, 139.5, 136.3, 132.1, 129.8, 128.4, 127.5, 125.4, 118.8, 117.8, 113.2.
(3) Results of mass spectrometry (ESI-TOF MS):
m/z=318.0 (M-H)$^-$.
(4) Results of purity measurement (HPLC):
Purity: 97.5 area %, retention time of 18.2 minutes.

Production Example of Polymerizable Monomer (11)

A polymerizable monomer (11) represented by the following structural formula (11) was produced according to the following scheme.

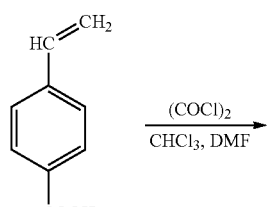

Formula (21)

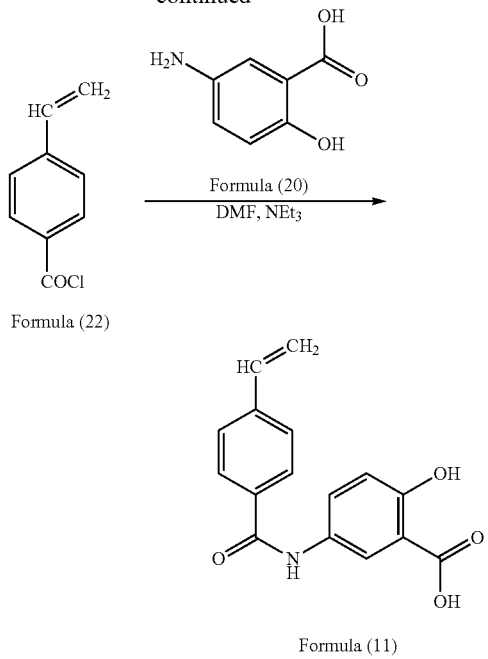

Formula (22)

Formula (11)

Into a reaction vessel fitted with a cooling pipe, a stirrer, a thermometer and a nitrogen feed pipe, 20 parts of formula-(21) 4-vinylbenzoic acid, 0.6 part of 4-tert-butylcatechol and 225 parts of chloroform were fed, and then cooled to 15° C. or below. While keeping the liquid temperature at 15° C. or below, 2.8 parts of dehydrated N,N-dimethylformamide was added, and then 87.4 parts of oxalyl chloride was dropwise added thereto. After its addition made dropwise, the liquid temperature was raised to room temperature, followed by stirring for 20 hours. After the reaction was completed, the solvent was evaporated off under reduced pressure, and then 340 parts of n-heptane was added. The organic layer formed was washed with ion-exchanged water, and this organic layer was dried with magnesium sulfuric anhydride, followed by evaporation of the solvent under reduced pressure to obtain a crude product of formula-(22) 4-vinylbenzoic acid chloride (21.8 parts).

Into a reaction vessel fitted with a cooling pipe, a stirrer, a thermometer and a nitrogen feed pipe, 24.1 parts of formula-(20) 5-aminosalicylic acid, 60 parts of dehydrated N,N-dimethylformamide and 22.1 parts of triethylamine were fed, and then stirred under ice cooling. To the solution obtained, while this was kept at 10° C. or below, a solution beforehand prepared by dissolving in 35 parts of chloroform 21.8 parts of the formula-(22) 4-vinylbenzoic acid chloride obtained above was dropwise added. After its addition made dropwise was completed, the liquid temperature was slowly returned to room temperature, where the reaction was carried out for 12 hours. After the reaction was completed, the reaction solution was poured into 500 parts of an aqueous 1 mol/liter hydrochloric acid solution, and the precipitate having come deposited was separated by filtration. The precipitate obtained was washed with an aqueous 1 mol/liter hydrochloric acid solution and with ion-exchanged water, and the resultant precipitate was separated by filtration and then dried under reduced pressure to obtain 32 parts of the polymerizable monomer (11) (yield: 88%).

That the polymerizable monomer obtained had the structure represented by the above formula was identified by using the instruments described previously. The results of analysis are shown below.

Results of Analysis of Polymerizable Monomer (11)

Figure 2:
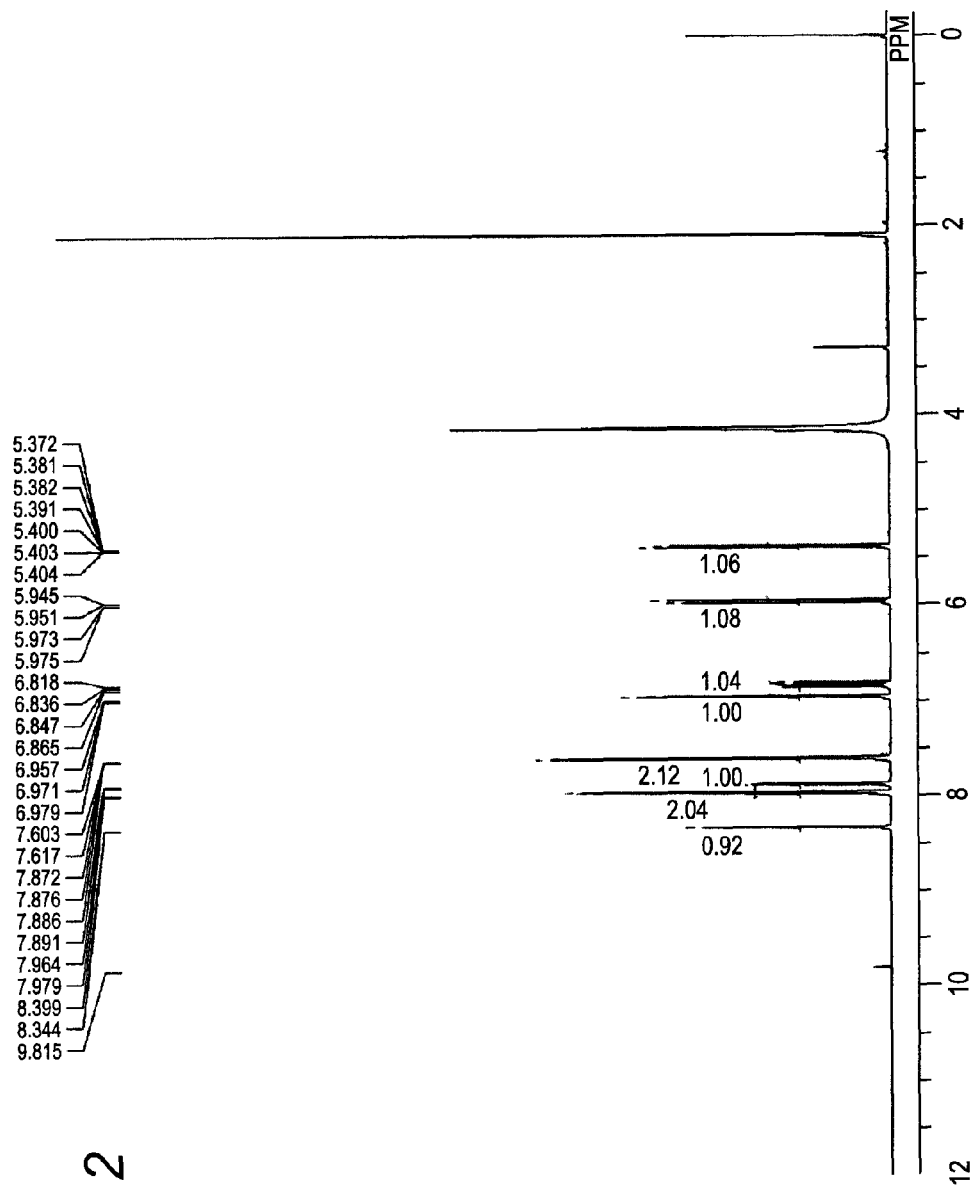
FIG. 2 is a chart showing $^1$H NMR spectrum of a polymerizable monomer (11) in acetone-$d_6$ and at room temperature and 400 MHz.

(1) Results of $^1$H NMR (400 MHz, acetone-d$_6$, 25° C.) (see FIG. 2):

δ [ppm]=8.34 (d, 1H), 7.97 (d, 2H), 7.8 (dd, 1H), 7.61 (d, 2H), 6.97 (d, 1H), 6.84 (dd, 1H), 5.96 (dd, 2H), 5.38 (dd, 1H).

(2) Results of $^{13}$C NMR (100 MHz, in deuterated acetone, 25° C.)

δ [ppm]=172.9, 166.8, 159.6, 141.9, 137.1, 135.1, 131.6, 130.0, 128.8, 127.2, 123.4, 118.1, 116.5, 113.2, 100.4, 97.4.

(3) Results of mass spectrometry (ESI-TOF MS): m/z=282.1 (M-H)$^-$.

(4) Results of purity measurement (HPLC):

Purity: 98.8 area %, retention time of 19.4 minutes.

Production Example of Polymerizable Monomer (16)

A polymerizable monomer (16) represented by the following structural formula (16) was produced according to the following scheme.

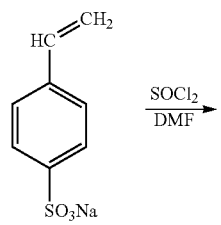

Formula (18)

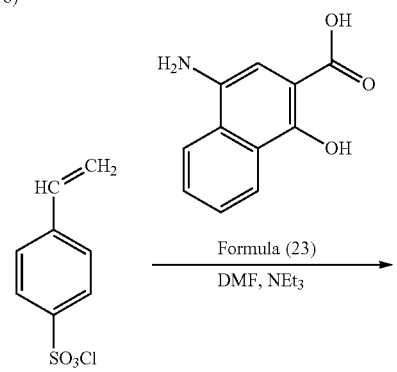

Formula (19)

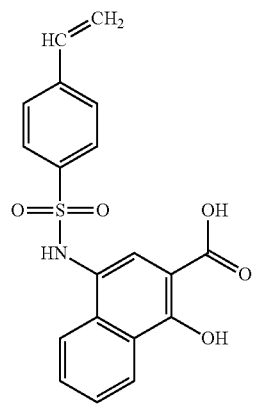

Formula (16)

Formula-(19) p-styrenesulfonic acid chloride was likewise produced by the process described in Production Example of Polymerizable Monomer (8).

Into a reaction vessel fitted with a cooling pipe, a stirrer, a thermometer and a nitrogen feed pipe, 10 parts of formula-(23) 4-amino-1-hydroxy-2-naphthoic acid, 106 parts of dehydrated N,N-dimethylformamide and 5 parts of triethylamine were fed, and then stirred under ice cooling. To the solution obtained, while this was kept at 5° C. or below, a solution beforehand prepared by dissolving in 15 parts of chloroform 10.3 parts of the formula-(19) p-styrenesulfonic acid chloride obtained above was dropwise added. After its addition made dropwise was completed, the liquid temperature was slowly returned to room temperature, where the reaction was carried out for 4 hours. After the reaction was completed, 270 parts of ethyl acetate was added, and the organic layer formed was washed with an aqueous 1 mol/liter hydrochloric acid solution and with ion-exchanged water. This organic layer was then dried with sodium sulfuric anhydride, followed by concentration of the solvent under reduced pressure and then reprecipitation with n-heptane. Thereafter, the precipitate formed was separated by filtration to obtain 8 parts of the polymerizable monomer (16) (yield: 46%).

That the polymerizable monomer obtained had the structure represented by the above formula was identified by using the instruments described previously. The results of analysis are shown below.

Results of Analysis of Polymerizable Monomer (16)

Figure 3:
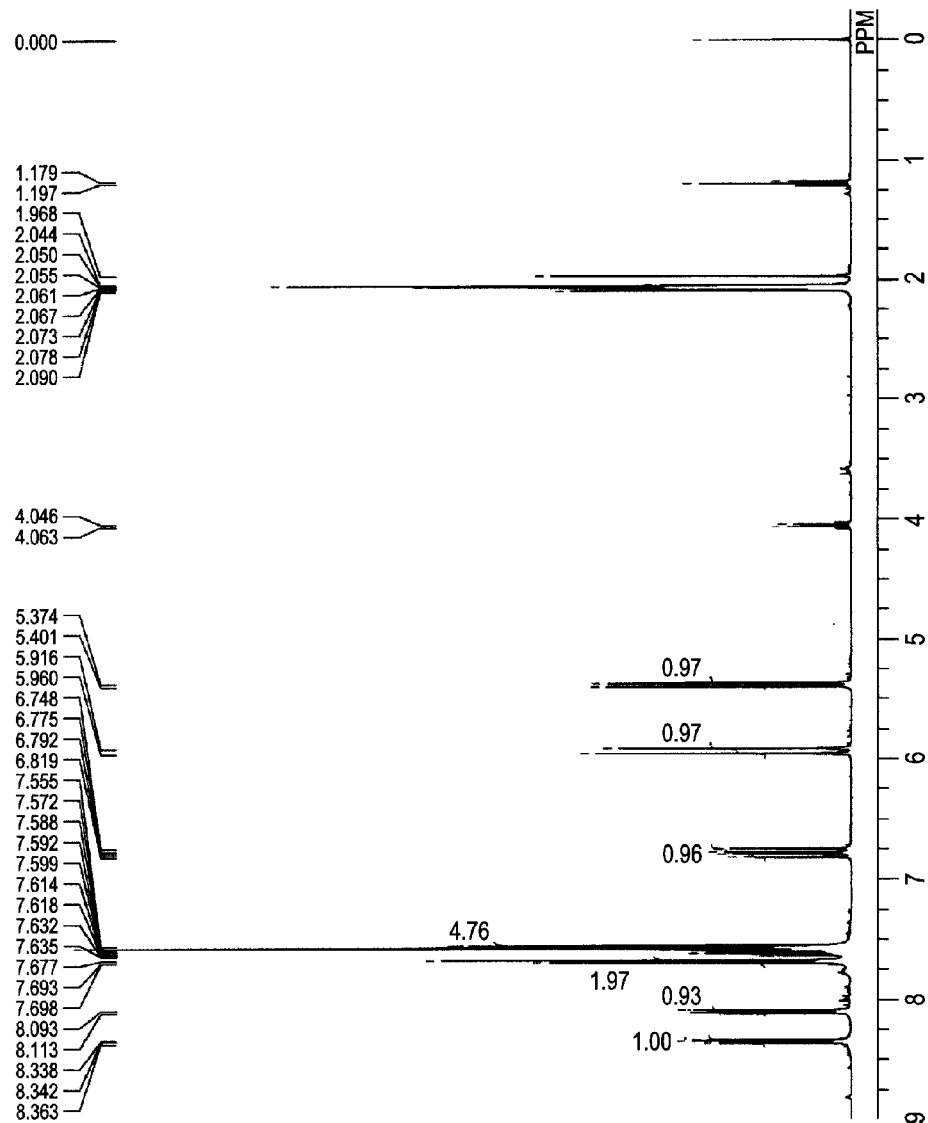
FIG. 3 is a chart showing $^1$H NMR spectrum of a polymerizable monomer (16) in acetone-$d_6$ and at room temperature and 400 MHz.

(1) Results of $^1$H NMR (400 MHz, acetone-d$_6$, 25° C.) (see FIG. 3):

δ [ppm]=8.35 (d, 1H), 8.10 (d, 1H), 7.69 (d, 2H), 7.64-7.56 (m, 5H), 6.78 (dd, 1H), 5.94 (d, 1H), 5.39 (d, 1H).

(2) Results of $^{13}$C NMR (100 MHz, acetone-d$_6$, 25° C.)

δ [ppm]=172.8, 161.0, 142.6, 139.9, 136.4, 135.6, 130.5, 128.6, 127.4, 127.1, 126.0, 124.9, 124.5, 124.4, 124.3, 117.6, 105.7.

(3) Results of mass spectrometry (ESI-TOF MS): m/z=368.1 (M-H)$^-$.

(4) Results of purity measurement (HPLC):

Purity: 97.8 area %, retention time of 18.3 minutes.

Production Examples of Other Polymerizable Monomers

The procedure of Production Examples of Polymerizable Monomers (8), (11) and (16) each was repeated, but to produce polymerizable monomers (9), (10), (12) to (15) and (17) which are each the formula-(1) polymerizable monomer. The polymerizable monomers produced are summarized in Table 1 below.

Example 2

Polymeric compounds of the present invention were produced in the following way.

Production Example of Polymeric Compound (A)

Into a reaction vessel fitted with a cooling pipe, a stirrer, a thermometer and a nitrogen feed pipe 100 parts of styrene, 19.6 parts of the polymerizable monomer (8), 7.2 parts of tert-butyl peroxyisopropyl carbonate and 290 parts of propylene glycol monomethyl ether acetate were fed, and nitrogen bubbling was carried out for 30 minutes. The reaction solution formed was heated at 145° C. for 8 hours in an atmosphere of nitrogen to complete polymerization reaction. The reaction solution obtained was cooled to room temperature, and thereafter the solvent was evaporated off under reduced pressure. The solid obtained was dissolved in acetone, and then re-precipitated twice with methanol. The precipitate obtained was separated by filtration, followed by drying under reduced pressure to obtain a polymeric compound (A).

The polymeric compound (A) obtained was analyzed by the analytical method described previously. The results are shown below. In the following, "St" in $^1$H NMR analysis stands for a signal due to a styrene unit, and "a" a signal due to the polymerizable monomer (8).

Results of Analysis of polymeric compound (A)

Figure 4:
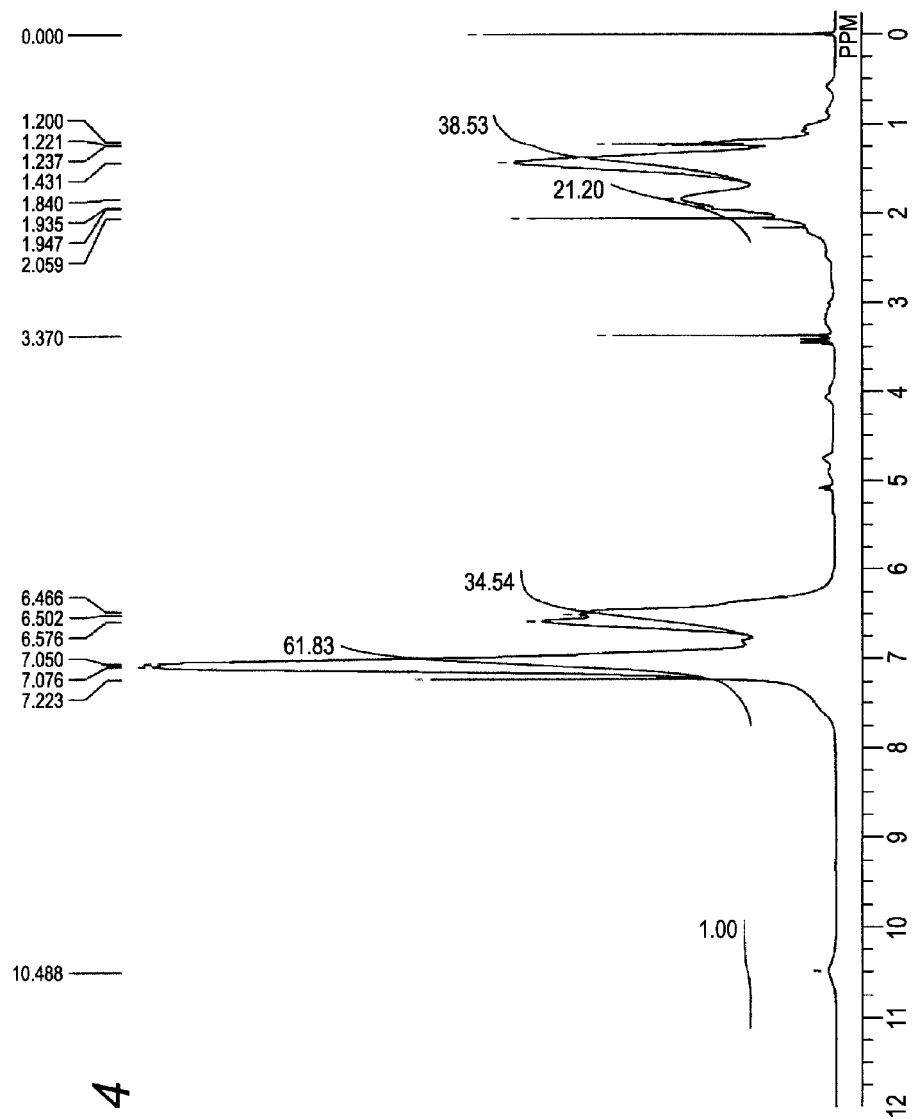
FIG. 4 is a chart showing $^1$H NMR spectrum of a polymeric compound (A) in CDCl$_3$ and at room temperature and 400 MHz.

(1) Results of $^1$H NMR (400 MHz, CDCl$_3$, 25° C.) (see FIG. 4):

δ [ppm]=10.5[brs, 1H(a)], 7.22-7.05[brs, 61.8H(St,a)], 6.58-6.47[brs, 34.5H(St,a)], 2.06-1.84[br, 21.2 (St,a)], 1.43-1.20[br, 38.5 (St,a)].

(2) Results of measurement of acid value: 27.4 mgKOH/g.

(3) Results of measurement of molecular weight (SEC): Weight-average molecular weight (Mw)=15,300.

From the above results, it was identified that the polymeric compound (A) obtained had therein the unit formed of the polymerizable monomer (8) in a content of 5 mol % in the whole monomer units.

Production Examples of Other Polymeric Compounds

The procedure of Production Example of Polymeric Compound (A) was repeated, but to produce polymeric compounds (B) to (O) each containing the formula-(3) unit. The polymeric compounds produced are summarized in Table 1 below.

Comparative Example 1

Polymeric compounds for comparison were produced in the following way.

Production Example of Polymeric Compound (P)

A polymeric compound (P) for comparison was produced in the same way as Production Example of Polymeric Compound (A) except that 19.6 parts of the polymerizable monomer (8) was changed for 11.1 parts of 2-acrylamido-2-methylpropanesulfonic acid. Its values of physical properties are shown in Table 1.

Production Example of Polymeric Compound (Q)

A polymeric compound (Q) for comparison was produced in the same way as Production Example of Polymeric Compound (A) except that 19.6 parts of the polymerizable monomer (8) was changed for 9.9 parts of 5-vinylsalicylic acid. Its values of physical properties are shown in Table 1.

[In Table 1, "Copolymer component I" indicates the polymerizable monomer used in synthesizing the polymeric compound. The numeral in "A" indicates the position of substitution with respect to the vinyl group in the formula (1).]

Example 3

Developing rollers of the present invention were produced in the following way.

Production Example of Developing Roller (1)

1) Surface Layer Composition Preparing Step:

What was composed as shown below were put to dispersion for 3 hours by means of a ball mill.

| | |
|---|---|
| Urethane coating material | 100 parts |
| (NIPPOLAN N5033, trade name; available from Nippon Polyurethane Industry Co., Ltd.) | |
| Polymeric compound (A) | 10 parts |
| Carbon black | 50 parts |
| (TOKA BLACK #7360SB, trade name; available from Tokai Carbon Co., Ltd.) | |
| Urethane particles | 6 parts |
| (ART PEARL C400, trade name; available from Negami Kogyo K.K.; average particle diameter: 15 μm) | |
| Methyl ethyl ketone | 1,000 parts |

To the fluid dispersion obtained, 10 parts of a modified tolylene diisocyanate (COLONATE L, trade name; available from Nippon Polyurethane Industry Co., Ltd.) was added as a curing agent to make up a surface layer composition.

2) Elastic Layer Forming Step:

A mandrel (made of stainless steel) of 8 mm in outer diameter was concentrically set in a cylindrical mold of 16 mm in inner diameter, and, as a material for a conductive elastic layer, liquid conductive silicone rubber (available from Dow Corning Toray Silicone Co., Ltd.; Asker-C hardness: 35 degrees; volume resistivity: 10×10$^9$ Ω·cm) was casted into it. Thereafter, this was heated for 20 minutes in a 130° C. oven to carry out molding. After demolding, the

TABLE 1

Polymerizable Monomer & Polymeric Compound of The Invention

| | | Copolymer components | | | | | | | | Compositional ratio | Acid value | |
|---|---|---|---|---|---|---|---|---|---|---|---|---|
| | | I | | | | | | | | | | |
| Polymeric compound | Polymerizable monomer | A | R$_1$ | a | b | c | d | II | III | (molar ratio) I:II:III | (mg-KOH/g) | Mw |
| (A) | (8) | 4-SO$_2$ | H | H | * | H | H | styrene | none | 5:95:0 | 27.4 | 15,300 |
| (B) | (8) | 4-SO$_2$ | H | H | * | H | H | styrene | none | 10:90:0 | 51.2 | 12,700 |
| (C) | (9) | 4-SO$_2$ | H | H | H | * | H | styrene | none | 5:95:0 | 26.4 | 14,900 |
| (D) | (10) | 4-SO$_2$ | H | H | H | H | * | styrene | none | 5:95:0 | 24.8 | 13,500 |
| (E) | (11) | 4-CO | H | H | * | H | H | styrene | none | 5:95:0 | 23.3 | 16,900 |
| (F) | (12) | 3-CO | H | H | * | H | H | styrene | none | 5:95:0 | 22.5 | 15,400 |
| (G) | (13) | 4-SO$_2$ | H | H | * | H | CH$_3$ | styrene | none | 5:95:0 | 25.2 | 17,400 |
| (H) | (14) | 4-SO$_2$ | H | H | * | H | SO$_3$H | styrene | none | 5:95:0 | 52.8 | 13,300 |
| (I) | (15) | 4-SO$_2$ | H | H | * | OCH$_3$ | H | styrene | none | 5:95:0 | 28.3 | 16,200 |
| (J) | (16) | 4-SO$_2$ | H | H | * | —C$_4$H$_4$— | | styrene | none | 5:95:0 | 22.7 | 17,800 |
| (K) | (17) | 4-CO | CH$_3$ | H | * | H | H | styrene | none | 5:95:0 | 24.1 | 17,800 |
| (L) | (8) | 4-SO$_2$ | H | H | * | H | H | styrene | acrylic acid | 5:90:5 | 49.1 | 14,400 |
| (M) | (8) | 4-SO$_2$ | H | H | * | H | H | styrene | methacrylic acid | 5:90:5 | 24.5 | 15,600 |
| (N) | (8) | 4-SO$_2$ | H | H | * | H | H | α-methyl styrene | n-butyl methacrylate | 5:90:5 | 23.7 | 13,800 |
| (O) | (8) | 4-SO$_2$ | H | H | * | H | H | styrene | N,N'-diethyl acrylamide | 5:90:5 | 24.6 | 18,200 |
| (P) | 2-acrylamido-2-methylpropanesulfonic acid | | | | | | | styrene | none | 5:95:0 | 22.9 | 13,500 |
| (Q) | 5-vinylsalicylic acid | | | | | | | styrene | none | 5:95:0 | 27.1 | 15,500 | molded product was subjected to secondary vulcanization for 4 hours in a 200° C. oven to obtain a roller with an elastic layer formed thereon (layer thickness: 4 mm).

3) Surface Layer Forming Step:

While the surface layer composition in the step 1 was stirred, the roller with the elastic layer thus formed was so coated thereon with the surface layer composition by dipping as to form a surface layer in a layer thickness of 20 µm. The wet coating formed was dried for 5 minutes in a 80° C. oven, followed by curing for 4 hours in a 140° C. oven to obtain a developing roller (1).

Production Examples of Developing Rollers (2) to (15)

Developing rollers (2) to (15) were produced in the same way as Production Example of Developing Roller (1) except that the polymeric compound (A) was changed for the polymeric compounds (B) to (O), respectively.

Comparative Example 2

Developing rollers for comparison were produced in the following way.

Production Example of Developing Roller (16)

A developing roller (16) for comparison was produced in the same way as Production Example of Developing Roller (1) except that the polymeric compound (A) was not added to the surface layer composition.

Production Example of Developing Roller (17)

A developing roller (17) for comparison was produced in the same way as Production Example of Developing Roller (1) except that the polymeric compound (A) was changed for a salicylic acid aluminum compound (BONTRON E-108, trade name; available from Orient Chemical Industries, Ltd.).

Production Example of Developing Roller (18)

A developing roller (18) for comparison was produced in the same way as Production Example of Developing Roller (1) except that the polymeric compound (A) was changed for the polymeric compound (P).

Production Example of Developing Roller (19)

A developing roller (19) for comparison was produced in the same way as Production Example of Developing Roller (1) except that the polymeric compound (A) was changed for the polymeric compound (Q).

Example 4

The charge characteristics of the polymeric compound of the present invention and those of the polymeric compound for comparison and salicylic acid aluminum compound were evaluated in the following way.

Evaluation of Charge Characteristics:

The charge characteristics were evaluated by measuring charge quantity with a cascade type charge quantity measuring instrument manufactured by KYOCERA Chemical Corporation, on a coating film formed by coating a conductive substrate with the polymeric compound or salicylic acid aluminum compound to be measured.

Figure 5:
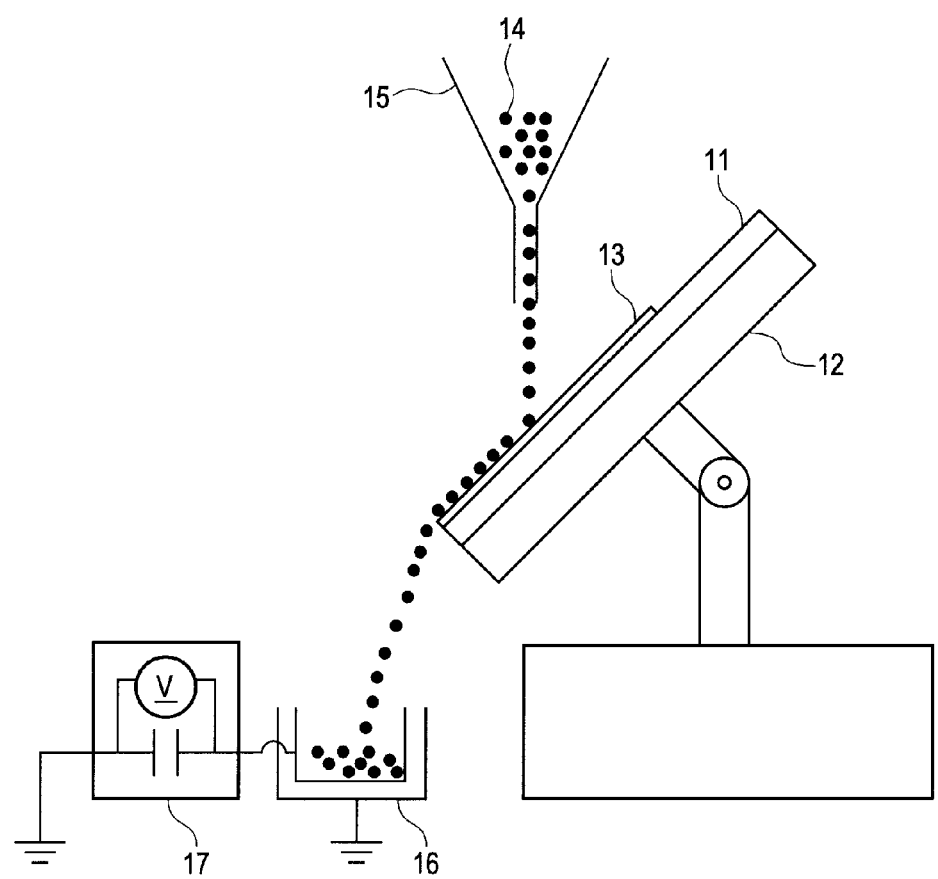
FIG. 5 is a view showing a cascade type charge quantity measuring instrument used to evaluate the charge characteristics of the polymeric compound of the present invention.

FIG. 5 is a diagrammatic view of the charge quantity measuring instrument used in the present evaluation. In FIG. 5, reference numeral 11 denotes the conductive substrate; 12, a substrate holder stand; 13, the polymeric compound (or salicylic acid aluminum compound) coating film; 14, a standard powder; 15, a standard powder feeder; 16, a standard powder receiver; and 17, an electrometer. A specific method of measurement with this instrument is as shown below.

The polymeric compound and, as a binder resin, polystyrene (weight-average molecular weight: 35,000, available from Sigma-Aldrich Corporation) were dissolved in methyl ethyl ketone, and the conductive substrate 11, made of aluminum, was coated by means of a wire bar with the solution obtained, followed by drying at 25° C. for 24 hours or more. At this stage, the amounts of the polymeric compound and binder resin were so controlled as to be in a proportion of 1:9 (in parts by mass). Also, the concentration of the coating solution and the type of the wire bar were so selected as for the coating film as to be 5 µm in layer thickness.

The conductive substrate 11 coated with the polymeric compound was attached to the substrate holder stand 12, and this substrate holder stand 12 was so fixed as for the conductive substrate 11 to be kept at an angle of inclination of 45°.

In an environment controlled at 25° C./45% RH and using as the standard powder 14 a manganese ferrite carrier (average particle diameter: 80 µm) available from Powdertech Co., the standard powder 14 was let flow from the standard powder feeder 15 over the coating film 13 at a flow rate of 15 g/min. Here, the flow path through which the standard powder 14 flows over the coating film 13 was kept so controlled as to be 20 mm in flow path length and 15 mm in flow path width.

4) The standard powder 14 having come into contact with the coating film 13 was electrostatically charged and then all collected in the standard powder receiver 16. The standard powder receiver 16 serves as Faraday cage, and the quantity of electric charges the standard powder 14 has received from the coating film 13 can be measured with the electrometer 17 connected. Meanwhile, the charge quantity of the coating film 13 is shown as an inverse sign of the charge quantity of the standard powder 14.

The charge characteristics of the polymeric compound or salicylic acid aluminum compound were evaluated by the charge quantity the coating film 13 has when 50 g of the standard powder 14 was let flow over it in the above charge quantity measuring method, and were judged according to the following criteria.

A: Very good (the charge quantity of the coating film is less than −125 nC).

B: Good (the charge quantity of the coating film is −125 nC or more to less than −100 nC).

C: Feasible for practical use (the charge quantity of the coating film is −100 nC or more to less than −75 nC).

D: Inferior (the charge quantity of the coating film is −75 nC or more).

As long as the charge quantity of the coating film is less than −100 nC, the charge characteristics thereof were judged to be good.

Example 5

The developing roller of the present invention or the developing roller for comparison was fitted to an evaluation-purpose copying machine (manufactured by CANON INC.; trade name: NP6035,) making use of a positively chargeable developer, where stated images were continuously copied on 15,000 sheets in an environment controlled at 32.5° C. and 80% RH, and thereafter evaluation was made on fog and image density.

Evaluation on Image Fog:

Reflectance (D1) at a solid white portion of a recording sheet on which images were formed and reflectance (D2) at a virgin portion of the same recording sheet were measured at 5 spots for each of these portions by using a white-light intensity meter TC-6DS/A, trade name, manufactured by Tokyo Denshoku Co., Ltd.), and an average value thereof was cal culated. The value of D1 minus D2 was taken as fog density, which was judged according to the following criteria.

A: Very good (the fog density is less than 1.0%.
B: Good (the fog density is 1.0% or more to less than 1.5%).
C: Feasible for practical use (the fog density is 1.5% or more to less than 2.0%).
D: Inferior (the fog density is 2.0% or more).

As long as the fog density is less than 1.5%, the evaluation on fog was judged to be good.

Evaluation of Image Density:

Reflection density at a solid black portion [OD(Bk)] of a recording sheet on which images were formed was measured at 5 spots of that portion by using a reflection densitometer (manufactured by Gretag Macbeth Ag.; trade name: RD918), and an average value thereof was calculated. The evaluation of image density was judged according to the following criteria.

A: Very good (the reflection density is 1.4 or more).
B: Good (the reflection density is 1.3 or more to less than 1.4).
C: Feasible for practical use (the reflection density is 1.2 or more to less than 1.3).
D: Inferior (the reflection density is less than 1.2).

As long as the reflection density is 1.3 or more, the evaluation of image density was judged to be good.

The evaluation of the charge characteristics of the polymeric compound of the present invention and those of the polymeric compound for comparison and salicylic acid aluminum compound and the evaluation on the image fog and image density attributable to the developing roller of the present invention and developing roller for comparison were made by the above evaluation methods. The results of evaluation are shown in Table 2.

TABLE 2

Results of valuation of
Polymeric Compound & Developing Roller of The Invention

| Developing roller No. | Polymeric compound | | | |
| --- | --- | --- | --- | --- |
| | Type | Charge characteristics | Fog | Image density |
| (1) | (A) | A | A | A |
| (2) | (B) | A | A | A |
| (3) | (C) | A | A | A |
| (4) | (D) | A | A | A |
| (5) | (E) | A | A | A |
| (6) | (F) | A | A | A |
| (7) | (G) | A | A | A |
| (8) | (H) | A | A | A |
| (9) | (I) | A | A | A |
| (10) | (J) | A | A | A |
| (11) | (K) | A | B | A |
| (12) | (L) | A | B | B |
| (13) | (M) | B | A | A |
| (14) | (N) | B | A | A |
| (15) | (O) | A | B | B |
| (16) | none | D | D | D |
| (17) | salicylic acid aluminum compound | C | C | C |
| (18) | (P) | C | C | C |
| (19) | (Q) | B | C | C |

As can be seen from Table 2, it has been ascertained that the polymeric compound of the present invention has superior charge characteristics and also that the incorporation thereof in the developing roller enables images to be obtained which have a high image density.

Example 6

Toners of the present invention were produced in the following way.

Production Example of Toner (1)

1) Polymerizable Monomer Composition Preparing Step:

What was composed as shown below was mixed and thereafter put to dispersion for 3 hours by means of a ball mill.

| | |
| --- | --- |
| Styrene | 82.0 parts |
| 2-Ethylhexyl acrylate | 18.0 parts |
| Divinylbenzene | 0.1 part |
| C.I. Pigment Blue 15:3 | 5.5 parts |
| Polar resin (saturated polyester resin, terephthalic acid-propylene oxide modified bisphenol A polycondensation product; number-average molecular weight (Mn): 6,000; acid value: 15 mg KOH/g) | 5.0 parts |
| Polymeric compound (A) | 1.0 part |

The fluid dispersion obtained was heated to 60° C. with stirring at 300 rpm, and thereafter 12.0 parts of ester wax (peak temperature of maximum endothermic peak in DSC measurement: 70° C.; number-average molecular weight (Mn): 704) and 3.0 parts of 2,2'-azobis(2,4-dimethylvaleronitrile) were added thereto to make up a polymerizable monomer composition.

2) Dispersion Stabilizer Preparing Step:

Into a 2-liter four-necked flask fitted with a high-speed stirrer TK-homomixer (manufactured by PRIMIX Corporation), 710 parts of ion-exchanged water and 450 parts of an aqueous 0.1 mol/liter sodium phosphate solution were introduced, and these were heated to 60° C. with stirring at 12,000 rpm. To the mixture obtained, 68.0 parts of an aqueous 1.0 mol/liter calcium chloride solution was slowly added to prepare an aqueous dispersion medium containing calcium chloride as a fine slightly water-soluble dispersion stabilizer.

3) Granulation and Polymerization Step:

Into the aqueous dispersion medium obtained, the polymerizable monomer composition prepared in the step 1 was introduced to carry out granulation for 15 minutes while keeping a number of revolutions of 12,000 rpm. Thereafter, the high-speed stirrer was changed for a stirrer having propeller stirring blades, and, at its internal temperature of 60° C., the polymerization was continued for 5 hours. Thereafter, the internal temperature was raised to 80° C., and the polymerization was further continued for 3 hours. After the polymerization reaction was completed, residual monomers were evaporated off at 80° C. under reduced pressure, followed by cooling to 30° C. to obtain a fine polymer particle fluid dispersion.

4) Washing and Drying Step:

The fine polymer particle fluid dispersion obtained was moved to a washing container, and diluted hydrochloric acid was added thereto with stirring to make adjustment of pH to 1.5. The resultant fluid dispersion was stirred for 2 hours, followed by solid-liquid separation by means of a filter to obtain fine polymer particles. This was introduced into 1.0 liter of ion-exchanged water and stirred to make up a fluid dispersion again, followed by solid-liquid separation by means of the filter. This operation was carried out three times, and thereafter the fine polymer particles having finally been obtained by solid-liquid separation were sufficiently dried by means of a 30° C. dryer to obtain toner particles.

5) External Addition Step:

In 100.0 parts of the toner particles (toner base particles) obtained, 1.0 part of hydrophobic fine silica powder (number-average particle diameter of primary particles: 7 nm) having been surface-treated with hexamethyldisilazane, 0.15 part of fine rutile titanium oxide powder (number-average particle diameter of primary particles: 45 nm) and 0.5 part of fine rutile titanium oxide powder (number-average particle diameter of primary particles: 200 nm) were dry-process mixed for 5 minutes by means of Henschel mixer (manufactured by Nippon Coke & Engineering Co., Ltd.) to obtain a toner (1).

Production Examples of Toners (2) to (15)

Toners (2) to (15) were obtained in the same way as Production Example of Toner (1) except that the polymeric compound (A) was changed for the polymeric compounds (B) to (O), respectively.

Production Example of Toner (16)

1) Mixing Step:

What was composed as shown below was put to dispersion for 24 hours by means of a ball mill to obtain 200 parts of a toner composition liquid mixture.

| | |
|---|---|
| Ethyl acetate | 100.0 parts |
| C.I. Pigment Blue 15:3 | 5.0 parts |
| Polar resin | 85.0 parts |
| (saturated polyester resin, polycondensation product of propylene oxide modified bisphenol A with phthalic acid; glass transition point Tg: 75.9° C.; weight-average molecular weight Mw: 11,000; number-average molecular weight Mn: 4,200; acid value: 11 mgKOH/g) | |
| Hydrocarbon wax | 9.0 parts |
| (Fischer-Tropsch wax; peak temperature of maximum endothermic peak in DSC measurement: 80° C.; weight-average molecular weight Mw: 750) | |
| Polymeric compound (A) | 1.0 part |

2) Dispersion Suspension Step:

What was composed as shown below was put to dispersion for 24 hours by means of a ball mill to dissolve carboxymethyl cellulose to obtain an aqueous medium. Calcium carbonate 20.0 parts (coated with acrylic-acid type copolymer) Carboxymethyl cellulose 0.5 part (trade name: CELLOGEN BS-H, available from Dai-ichi Kogyo Seiyaku Co., Ltd.)

Ion-exchanged water 99.5 parts 1,200 parts of the aqueous medium obtained was put into TK-homomixer (manufactured by PRIMIX Corporation), and stirred rotating a rotating blade at a peripheral speed of 20 m/sec, during which 1,000 parts of the above toner composition fluid mixture was introduced thereinto. These were stirred for 1 minute while keeping temperature constantly at 25° C., to obtain a suspension.

3) Solvent Removal Step:

2,200 g of the suspension obtained in the dispersion suspension step was stirred by means of Full-zone blade (manufactured by Kobelco Eco-Solutions Co., Ltd.) at a peripheral speed of 45 m/min, during which, keeping the temperature constantly at 40° C., the gaseous phase on the suspension liquid level was forcedly sucked up by using a blower, to start to remove the solvent. In that course, after 15 minutes from the start of solvent removal, 75 parts of ammonia water diluted to 1% was added as an ionic substance. Subsequently, after 1 hour from the start of solvent removal, 25 parts of the like ammonia water was added. Subsequently, after 2 hours from the start of solvent removal, 25 parts of the like ammonia water was added. Finally, after 3 hours from the start of solvent removal, 25 parts of the like ammonia water was added, thus 150 g of the dilute ammonia water was added in total. Further, keeping the liquid temperature at 40° C., the system was held for 17 hours from the start of solvent removal. Thus, a toner fluid dispersion was obtained in which the solvent (ethyl acetate) was removed from suspended particles.

4) Washing and Dehydration Step:

To 300 parts of the toner fluid dispersion obtained in the solvent removal step, 80 parts of 10 mol/liter hydrochloric acid was added, followed by further addition of an aqueous 0.1 mol/liter sodium hydroxide solution to carry out neutralization treatment. Thereafter, washing with ion-exchanged water by suction filtration was repeated four times to obtain a toner cake. The toner cake thus obtained was dried by means of a vacuum dryer, followed by sifting through a 45-µm mesh sieve to obtain toner base particles.

Subsequent procedure in Production Example of Toner (1) was repeated to produce a toner (16).

Comparative Example 3

Toners for comparison were produced in the following way.

Production Example of Toner (17)

A toner (17) for comparison was produced in the same way as Production Example of Toner (1) except that the polymeric compound (A) was not added.

Production Example of Toner (18)

A toner (18) for comparison was produced in the same way as Production Example of Toner (1) except that the polymeric compound (A) was changed for a salicylic acid aluminum compound (BONTRON E-108, trade name; available from Orient Chemical Industries, Ltd.).

Production Example of Toner (19)

A toner (19) for comparison was produced in the same way as Production Example of Toner (1) except that the polymeric compound (A) was changed for the polymeric compounds (P).

Production Example of Toner (20)

A toner (20) for comparison was produced in the same way as Production Example of Toner (1) except that the polymeric compound (A) was changed for the polymeric compounds (Q).

Example 7

The particle diameter and particle size distribution of the toner of the present invention and those of the toner for comparison were measured in the following way Measurement of particle size distribution of toner: COULTER MULTISIZER (manufactured by Beckman Coulter, Inc.) was used, and an interface (manufactured by Nikkaki Bios Co.) that outputs number distribution and volume distribution and a personal computer were connected. As an aqueous electrolytic solution, ISOTON R-II (available from Beckman Coulter, Inc.) was used.

To 100 ml to 150 ml of the above aqueous electrolytic solution, 2 mg to 20 mg of a measuring sample (toner) was added. The electrolytic solution in which the sample was suspended was subjected to dispersion treatment for about 1 to 3 minutes in an ultrasonic dispersion machine. The volume and number of toner particles with particle diameters of 2.0 µm or more to 64.0 µm or less were measured with the above COULTER MULTISIZER, using its 100 µm aperture. The data obtained were apportioned to 16 channels to determine the weight-average particle diameter D4, the number average particle diameter D1 and the value of D4/D1.

Example 8

The charge quantity of the toner of the present invention and that of the toner for comparison were measured in the following way.

Figure 6:
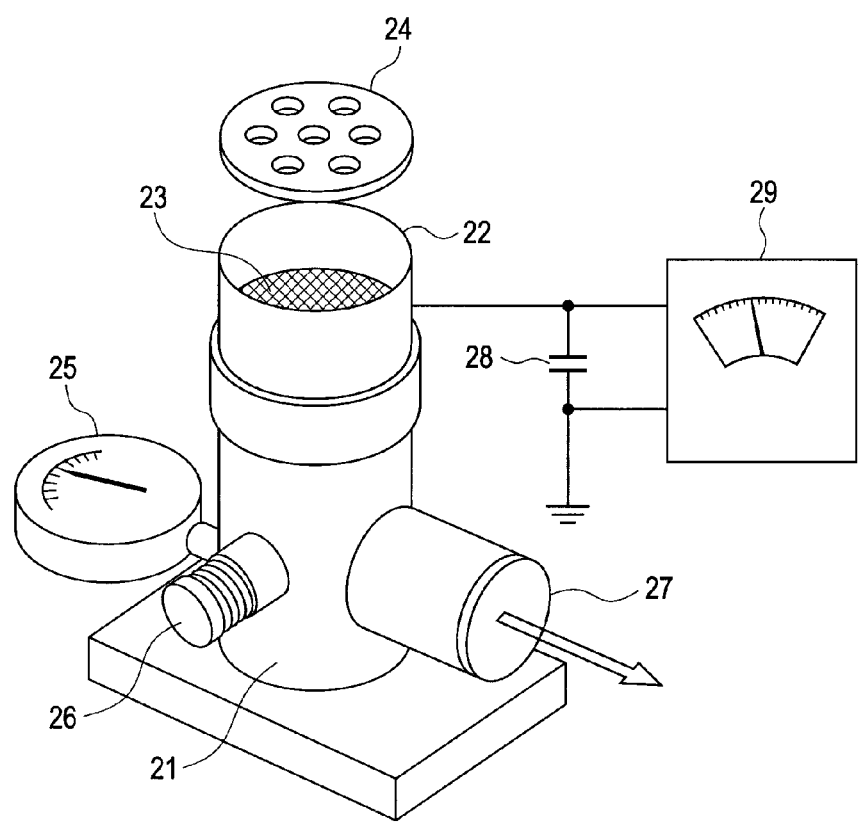
FIG. 6 is a view showing the construction of an instrument for measuring the triboelectric charge quantity of the toner of the present invention.

Evaluation of Charge Quantity of Toner:

To measure triboelectric charge quantity, 0.5 g of the toner and 9.5 g of a carrier were put into a 50 cc plastic container and then this was left to stand overnight in a normal temperature and normal humidity environment (23° C./60% RH). Thereafter, this was shaken for a stated time (10 seconds and 300 seconds each) at a shaking speed of 200 times per minute, and the triboelectric charge quantity of what was thus shaken was measured with an instrument shown in FIG. 6.

About 0.3 g of the toner the triboelectric charge quantity of which was to be measured was put into a measuring container 22 made of a metal and to the bottom of which a conductive screen 23 of 500 meshes (mesh opening: 25 μm) was attached, and the container was covered with a lid 24 made of a metal. The total mass of the measuring container 22 at this point was expressed as W1 (g). Next, in a suction device 21 (made of an insulating material at least at the part coming into contact with the measuring container 22), air was sucked from a suction opening 27 and an air-flow control valve 26 was operated to control the pressure indicated by a vacuum indicator 25, to be −2.0 kPa (gauge pressure). In this state, suction was carried out for 2 minutes to remove the toner by suction. The potential indicated by an electrometer 29 at this point was expressed as V (volt). Here, reference numeral 28 denotes a capacitor, whose capacitance was expressed as C (μF). The total mass of the measuring container after the suction was expressed as W2 (g). The triboelectric charge quantity (μC/g) of this toner was calculated according to the following expression.

Triboelectric charge quantity $(\mu C/g) = (C \times V)/(W1 - W2)$.

The evaluation of charge quantity was judged according to the following criteria. In working examples, negatively chargeable toners were prepared.

A: Very good (the triboelectric charge quantity is −20.0 μC/g or less).

B: Good (the triboelectric charge quantity is −10.0 μC/g to −19.9 μC/g).

C: Feasible for practical use (the triboelectric charge quantity is −5.0 μC/g to −9.9 μC/g).

D: Inferior (the triboelectric charge quantity is −4.9 μC/g or more).

As long as the triboelectric charge quantity is −10.0 μC/g or less, the toner was judged to have good charge characteristics.

Example 9

The reverse-polarity toner quantity of the toner of the present invention and that of the toner for comparison were measured in the following way.

Evaluation on Reverse-Polarity Toner Quantity:

The reverse-polarity toner quantity (quantity of toner with reverse polarity) was measured with E-SPART Analyzer EST-3, manufactured by Hosokawa Micron Corporation, and the number of particles of reverse-polarity toner (positive-polarity toner) that was based on the total number of toner particles was measured. To make the measurement, 0.5 g of the toner and 9.5 g of a carrier were put into a 50 cc plastic container and then this was left to stand overnight in a normal temperature and normal humidity environment (23° C./60% RH). Thereafter, this was shaken for 5 minutes at a shaking speed of 200 times per minute, and the measurement was made on what has been thus shaken.

The evaluation on the reverse-polarity toner quantity was judged according to the following criteria.

A: Very good (any reverse-polarity toner is not present).

B: Good (the reverse-polarity toner is in a proportion of less than 5%).

C: Feasible for practical use (the reverse-polarity toner is in a proportion of 5% or more to less than 15%).

D: Inferior (the reverse-polarity toner is in a proportion of 15% or more).

As long as the reverse-polarity toner is in a proportion of less than 5%, the toner was judged to have good charge characteristics.

The evaluation of particle size distribution and charge quantity and evaluation on reverse-polarity toner quantity of the toners of the present invention and toners for comparison thus produced were made by the above evaluation methods. The results of evaluation are shown in Table 3.

TABLE 3

Results of valuation of Toner of The Invention

| Toner No. | Polymeric compound | Toner production process | Particle size distribution Av. particle diam.* (μm) | D4/D1 | Toner charge quantity Shaking 10 sec. | 300 sec. | Reverse = polarity toner quantity |
|---|---|---|---|---|---|---|---|
| (1) | (A) | SusPoly | 7.2 | 1.25 | A | A | A |
| (2) | (B) | SusPoly | 6.4 | 1.34 | A | A | A |
| (3) | (C) | SusPoly | 7.0 | 1.22 | A | A | A |
| (4) | (D) | SusPoly | 7.1 | 1.24 | A | A | A |
| (5) | (E) | SusPoly | 7.0 | 1.23 | A | A | A |
| (6) | (F) | SusPoly | 7.5 | 1.30 | A | A | A |
| (7) | (G) | SusPoly | 7.3 | 1.29 | A | A | A |
| (8) | (H) | SusPoly | 6.5 | 1.35 | A | A | A |
| (9) | (I) | SusPoly | 7.4 | 1.22 | A | A | A |
| (10) | (J) | SusPoly | 7.5 | 1.28 | A | A | A |
| (11) | (K) | SusPoly | 6.9 | 1.25 | A | A | B |
| (12) | (L) | SusPoly | 6.3 | 1.36 | A | A | B |
| (13) | (M) | SusPoly | 6.7 | 1.22 | B | A | A |
| (14) | (N) | SusPoly | 6.6 | 1.24 | B | A | A |
| (15) | (O) | SusPoly | 7.4 | 1.21 | A | A | B |
| (16) | (A) | SusGran | 7.1 | 1.27 | A | A | A |
| (17) | none | SusPoly | 7.1 | 1.31 | D | D | D |
| (18) | salicylic acid aluminum compound | SusPoly | 7.3 | 1.23 | B | B | C |
| (19) | (P) | SusPoly | 7.4 | 1.25 | C | B | C |
| (20) | (Q) | SusPoly | 7.0 | 1.28 | C | A | C |

SusPoly: suspension polymerization
SusGran: suspension granulation
*Weight-average particle diameter (D4)

As can be seen from Table 3, it has been ascertained that the toner of the present invention has a high charging rise speed, shows a high saturated charge quantity, and at the same time can keep the reverse-polarity toner from forming.

INDUSTRIAL APPLICABILITY

The toner of the present invention makes use of as the charge control agent the polymeric compound obtained by the formula-(1) polymerizable monomer, and the present polymeric compound can also be utilized as a water-absorptive polymer and used as a proton-conducting film of fuel cells or the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-074835, filed Mar. 30, 2011 and Japanese Patent Application No. 2011-074551, filed Mar. 30, 2011, which are hereby incorporated by reference herein in their entirety.

REFERENCE SIGNS LIST 11 conductive substrate
12 substrate holder stand
13 polymeric compound coating film
14 standard powder
15 standard powder feeder
16 standard powder receiver
17 electrometer
21 suction device
22 measuring container
23 conductive screen
24 lid
25 vacuum indicator
26 air-flow control valve
27 suction opening
28 capacitor
29 electrometer

The invention claimed is:

1. A toner comprising a binder resin, a colorant and a charge control agent, wherein
the charge control agent comprises a polymeric compound containing at least one unit represented by the following formula (3):

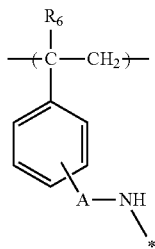

Formula (3)

wherein $R_6$ represents a hydrogen atom or an alkyl group; A represents —CO— or —SO$_2$—; and the moiety represented by the formula (3) is, at the part shown by an asterisk *, linked to a moiety represented by the following formula (2), at any position of a, b, c or d thereof;

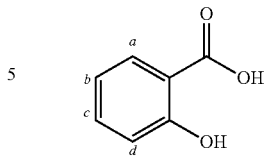

Formula (2)

wherein the sites among a, b, c and d at which the moiety represented by the formula (2) is not linked to the moiety represented by the formula (3) each has a hydrogen atom or a substituent selected from the group consisting of an alkyl group, an alkoxy group and a sulfonic acid group, or any of which may connect at mutually adjoining positions to form a ring.

2. The toner according to claim 1, which is produced by a suspension polymerization process.

3. The toner according to claim 1, which is produced by a suspension granulation process.

4. The toner according to claim 1, which is a copolymer of the unit represented by the formula (3) and at least one unit represented by the following formula (4):

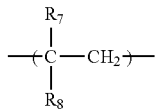

Formula (4)

wherein $R_7$ represents a hydrogen atom or an alkyl group; and $R_8$ represents a phenyl group, a carboxyl group, a carboxylate group or a carboxylic acid amide group.

5. The toner according to claim 1, wherein the unit represented by the formula (4) is a styrene derivative unit or an acrylate derivative unit.

6. The toner according to claim 1, wherein the polymeric compound has a weight-average molecular weight of from 3,000 to 100,000.

* * * * *